United States Patent
Bamba et al.

[11] Patent Number: 6,147,488
[45] Date of Patent: Nov. 14, 2000

[54] MEASUREMENT METHOD OF TIME DEPENDENT MAGNETIC REMANENCE IN A RECORDING MEDIUM

[75] Inventors: Yasuo Bamba; Iwao Okamoto; Kazunori Yamanaka; Wataru Yamagishi, all of Kawasaki, Japan

[73] Assignee: Fujitsu Limited, Kawasaki, Japan

[21] Appl. No.: 09/049,236

[22] Filed: Mar. 27, 1998

[30] Foreign Application Priority Data

Sep. 30, 1997 [JP] Japan .................................. 9-266891

[51] Int. Cl.$^7$ ............................. G01N 27/76; G01R 33/12
[52] U.S. Cl. ................................. 324/210; 360/31; 365/58
[58] Field of Search .................................. 324/210, 211, 324/212, 239, 262; 360/31, 53; 369/53, 58

[56] References Cited

U.S. PATENT DOCUMENTS 4,641,093   2/1987   Melgui et al. ............................. 324/239

FOREIGN PATENT DOCUMENTS 63-246688   10/1988   Japan .

Primary Examiner—Walter E. Snow
Attorney, Agent, or Firm—Greer, Burns & Crain, Ltd.

[57] ABSTRACT

A testing method for a magnetic recording medium which is magnetized measures variation of magnetization with the passage of time and evaluates the magnetic recording medium over its life. The method includes the steps of recording a first pattern at a density to be guaranteed in the magnetic recording medium, the first pattern having a difference between the sum total of areas of +bits and the sum total of areas of −bits, measuring remanence of the first pattern with the passage of time, and evaluating the magnetic recording medium over its life based on a measurement result.

10 Claims, 16 Drawing Sheets

X1: BIT LENGTH OF BIT "1"

X2: BIT LENGTH OF BIT "2"

a: WIDTH OF MAGNETIZATION TRANSITION REGION

X1: BIT LENGTH OF BIT "1"
X2: BIT LENGTH OF BIT "2"
a: WIDTH OF MAGNETIZATION TRANSITION REGION

TIME-DEPENDENT REMANENCE OF UNIFORM
MAGNETIZATION : DC-ERASED PATTERN
REGRESSION: ——— y=0.00018995-1.3576e-06log(t)

TIME-DEPENDENT REMANENCE OF UNIFORM
MAGNETIZATION : DC-ERASED PATTERN
REGRESSION: ———— y=0.00023171-8.1789e-06log(t)

TIME-DEPENDENT REMANENCE OF UNIFORM
MAGNETIZATION : DC-ERASED PATTERN
REGRESSION(REGION 1): ———— y=1-0.0071469log(t)
REGRESSION(REGION 2): ———— y=1-0.035298log(t)

TIME-DEPENDENT REMANENCE OF UNIFORM
BIT PATTERN : 300k/150kfci, REGION 1
REGRESSION: ——— $y = 2.3279e\text{-}05 - 1.1971e\text{-}06 \log(t)$ TIME-DEPENDENT REMANENCE OF BIT PATTERN :
300k/150kfci, REGION 2
REGRESSION: ——— $y = 5.9424e\text{-}05 - 5.7627e\text{-}06 \log(t)$ TIME-DEPENDENT REMANENCE OF BIT PATTERN :
300k/150kfci,REGION 3
REGRESSION: ——— y=-0.0014863+0.0002564log(t)

TIME-DEPENDENT REMANENCE OF BIT PATTERN :
300k/150kfci,REGION 4
REGRESSION: ——— y=0.00016479-2.3719e-05log(t)

REVERSAL TIME CONSTANT OF TIME-DEPENDENT REMANENCE FOR DC-ERASED PATTERN, 1ST-TIME REGION

REVERSAL TIME CONSTANT OF REMANENCE TIME-DECAY
FOR 300/150kfci BIT PATTERN, 1ST-TIME REGION

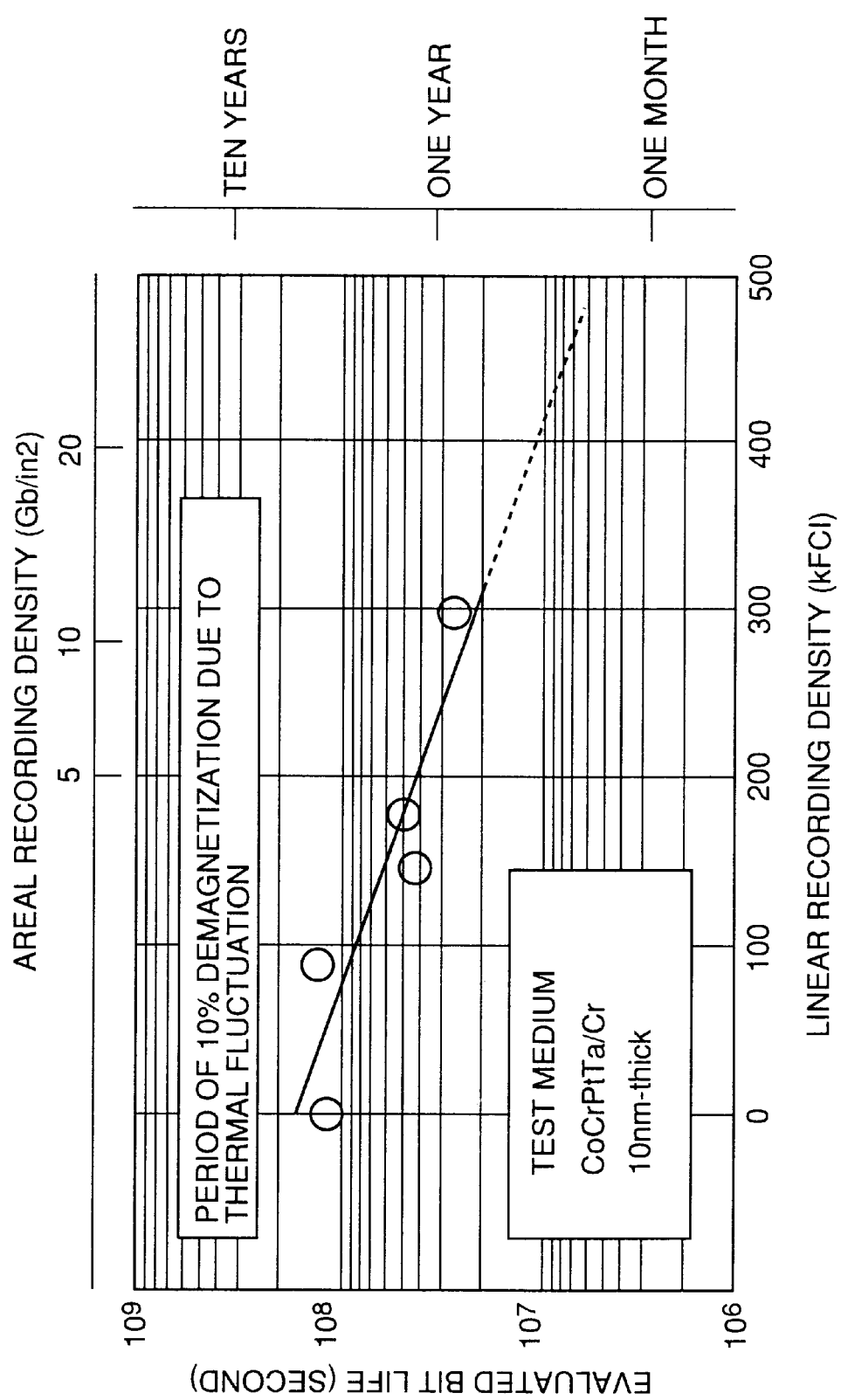

MEASUREMENT METHOD OF TIME DEPENDENT MAGNETIC REMANENCE IN A RECORDING MEDIUM

BACKGROUND OF THE INVENTION (1) Field of the Invention

The present invention generally relates to a testing method of a magnetic recording medium and a measurement method of a time constant of remanence thermal decay in a magnetized sample, and more particularly to a testing method of a magnetic recording medium to evaluate a life of record on the magnetic recording medium with a predetermined recording density and a method for measuring a time constant of remanence thermal decay in a magnetized sample.

In recent years, the recording density on the hard disk unit is being increased at a rate of about 60% a year. It is expected that the recording density in the longitudinal recording will reach to the upper limit in the near future. This is based on the reason that the higher the recording density on the magnetic recording medium the easier the more likely the occurrence of superparamagnetization due to thermal fluctuation.

Thus, it is expected that a magnetic recording unit to which the magnetic recording medium is set is required to be given a guarantee for a life of recorded bits (referred to as a bit record life). A technique for evaluating the bit record life for the magnetic recording medium is important.

Thus, it is necessary to improve the technique for evaluating the bit record life and to establish a method for guaranteeing the bit record life for the hard disk unit.

(2) Description of the Related Art

In accordance with various detection method, a magnetic recording medium in which a remarkable relaxation of magnetization due to thermal fluctuation be recognized in a short evaluating period such as a few days or a few weeks can be easy to test. For example, there is a method for reproducing recorded contents at predetermined intervals from a hard disk in which a predetermined file is recorded and detecting omission of the recorded contents. There is also a method for evaluating a hard disk by detecting reproduction output at predetermined intervals or by observation of the magnetic recording medium using a magnetic force microscope after signals are recorded in the magnetic recording medium using a read-write tester.

In addition, as a testing method for a test body having a long record life, in general, there is an accelerated life test. In the accelerated life test, the change, with the passage of short time, of the state of the test body at elevated temperatures is measured. As a result, the change, with the passage of long time, of the state of the test body at the room temperature can be estimated in a short time.

However, since the magnetic recording medium is formed of a magnetic thin film, such an accelerated life test can not applied to the magnetic recording medium. That is, the product (Ku×Va) of an anisotropy energy constant (Ku) of each of magnetic particles forming the magnetic thin film and an activation volume (Va) which is a unit of the magnetization reversal is an increasing function (Ku×Va=F(T)) with respect to temperature T, so that the energy barrier could not lowered as expected. Thus, it is difficult to accelerate a shrinkage of record life of the magnetic recording medium by elevating the temperature, so that the accelerated life test can not be applied to magnetic recording medium.

Thus, in order to evaluate the magnetic recording medium having the long record life, responses to the thermal fluctuation should be measured for a long time, and the tendency of relaxation should be detected based on the characteristic of the measured responses. The record life can then be evaluated.

For example, a sample piece of the magnetic recording medium is applied with the saturation magnetization in a direction, and the time response of the remanence (residual magnetization) is then measured after the external magnetic field is removed. To measure the remanence, for example, a vibrating sample magnetometer (VSM) or a superconducting quantum interference device (SQUID) is used.

Although the vibrating sample magnetometer has a low measurement sensitivity, the vibrating sample magnetometer can measure the remanence of small samples piled up. From the view point of accurate measurement, it is preferable to use the superconducting quantum interference device for the measurement.

In the superconducting quantum interference device (SQUID), the measurement is performed under a condition that the sample is maintained at the room temperature. The applied magnetic field is removed and the residual magnetic moment is measured as a function of time. Usually, the measurement is continued for several hours or a few days, or at most about one month. The measurement data is used to extrapolate the amount of relaxation due to thermal fluctuation.

From many studies, it is known that the remanence is substantially logarithmically varied with the passage of time. Based on this magnetic relaxation characteristic, the record life can be relatively accurately evaluated.

The above mentioned conventional method is practical for the test of the magnetic recording medium. However, the conventional method can be used only for uniform magnetization. It is not clear what degree of high density the recording can be performed at. The method for measuring the variation of the remanence in uniform magnetized pattern with the passage of time can not be substituted for a method for evaluating the bit record life. This is because of the following reasons. First, the state of magnetic record in a bit pattern differs from the state of magnetic record in a uniform magnetic pattern. Second, in the bit pattern, the demagnetizing field is strong so that the bit magnetization may be easily reversed. Thus, the magnetic relaxation of the bit pattern is greater than that of the uniform magnetizing pattern.

A simulation experiment based on a virtual magnetic particle structure which is suitable for calculation has been proposed by S. H. Charap et al. However, simulation experiments so far can not correctly reflect the characteristic of an actual medium. In addition, the theoretical calculation based on an actual structure of a medium has not yet sufficiently progressed.

That is, the conventional testing method for the magnetic recording medium has the following disadvantages.

First, a bit pattern suitable for the evaluation of the bit record life in a case where bits are magnetically recorded at a linear density at which the performance should be guaranteed has not yet been known. That is, the bit pattern includes two types of magnetizing directions. Although there are magnetized bits having two magnetizing directions microscopically, a difference between the total amount of magnetization in one of the directions and the total amount of magnetization in the other one of the directions appears microscopically. This fact is not considered in the conventional evaluation method.

Second, although it is known that the time response characteristic regarding the magnetic relaxation due to the thermal fluctuation is represented by a monotonously decreasing curve, the sequential variation of the magnetization under a condition in which the characteristic regarding the relaxation time is changed (the rate of the variation of the remanence with the passage of time) can not be processed in accordance with the conventional method. That is, in a case where the material characteristic parameters peculiar to material and a structure are extracted and the bit record life is obtained considering a state where the phenomenon of the magnetic relaxation followed by the statistical fluctuation in principle be transiently varied, a new technology is required.

Third, in a case where the magnetic relaxation of a bit pattern due to the thermal fluctuation is measured, a successful method for evaluating characteristic with the arrangement of bit pattern has not yet been obtained at all. A method for selecting information items provided with measurement points which are measured in accordance with the bit arrangement and extracting contents regarding the type of bit from the measurement data is needed. However, there is not such a method.

Fourth, a technique which relates the rate variation of the remanence in the bit cell with the passage of time to the bit record life has not yet been proposed. In this technique, the bit record life is obtained by using the fluctuation characteristic, obtained as the result of the measurement of the uniform magnetization, logarithmically varying with the passage of time (the conventional technique). This technique is needed for the evaluation of the bit record life.

SUMMARY OF THE INVENTION

Accordingly, a general object of the present invention is to provide a novel and useful method for testing a magnetic recording medium and method for measuring a magnetizing time constant of a magnetized piece in which the disadvantages of the aforementioned prior art are eliminated.

A specific object of the present invention is to provide a method which can accurately evaluate the record life of an actual magnetic recording medium.

The above objects of the present invention are achieved by a testing method of a magnetic recording medium which is magnetized, for measuring variation of magnetization with the passage of time and evaluating life of record on the magnetic recording medium, the method comprising the steps of: (a) recording a first pattern at a density to be guaranteed in the magnetic recording medium, the first pattern having a difference between the sum total of areas of +bits and the sum total of areas of −bits; (b) measuring remanence of the first pattern with the passage of time; and (c) evaluating the life of record on the magnetic recording medium based on a measurement result obtained in step (b).

According to the present invention, since the first pattern in which the sum total of areas of +bits differs from the sum total of areas of −bits is recorded on the magnetic recording medium at a density to be guaranteed, the magnetization can be measured. The remanence of the recording medium in which the magnetization pattern is actually recorded can be measured. Thus, the record life of an actual magnetic recording medium can be accurately evaluated.

The above step (c) may comprise the steps of: (c-1) obtaining a characteristic of transient response of the remanence based on the measurement result; and (c-2) obtaining a time constant of magnetization reversal based on the characteristic transient response of the remanence obtained in the step (c-1), wherein the life of record is evaluated based on the time constant of magnetization reversal obtained in the step (c-2).

According to this aspect of the present invention, since the life of record is evaluated based on the variation of the time constant of magnetization reversal, the life of record depending on the magnetic relaxation due to the thermal fluctuation can be evaluated. Thus, the accurate evaluation of the life of record can be obtained.

The above time constant of magnetization reversal may be obtained in each of a plurality of different periods. In this case, the above step (c) further comprises a step of: (c-3) measuring variation of the time constant of magnetization reversal with the passage of time in each of the plurality of different periods, wherein the life of record is evaluated based on the variation of the time constant of magnetization reversal with the passage of time in each of the plurality of different periods.

According to this aspect of the present invention, the life of record is evaluated based on the variation of the time constant of magnetization reversal in each of the plurality of different periods, so that the life of record depending on the magnetic relaxation due to the thermal fluctuation in each of the periods can be evaluated. Thus, the more accurate evaluation of the life of record can be obtained.

The above objects of the present invention are also achieved by a testing method of a magnetic recording medium which is magnetized, for measuring variation of magnetization with the passage of time and evaluating life of record on the magnetic recording medium, the method comprising the steps of: (a) recording a first pattern and a second pattern in the magnetic recording medium, the first pattern having a difference between the sum total of areas of +bits and the sum total of areas of −bits, the second pattern having a uniform magnetization; (b) measuring remanence of the first and second patterns with the passage of time; and (c) evaluating the life of record on the magnetic recording medium based on measurement results of the remanence time response of the first and second patterns obtained in step (b).

According to the present invention, since the record life of the magnetic recording medium is evaluated based on the remanence time response of the first and second patterns, the bit record life can be evaluated.

The above step (c) may comprises the steps of: (c-1) obtaining a characteristic of transient response of the remanence of each of the first and second patterns based on the measurement results; (c-2) obtaining a time constant of magnetization reversal based on the characteristic transient response of the remanence of each of the first and second patterns; and (c-3) obtaining relaxation time of the second pattern, wherein the life of record is evaluated based on both a ratio of the time constant of magnetization reversal of the first pattern to the time constant of magnetization reversal of the second pattern and the relaxation time of the second pattern.

According to this aspect of the present invention, the magnetic relaxation time obtained from the second pattern which is the uniform magnetization is multiplied by the ratio of the time constant of magnetization reversal of the first pattern to the time constant of magnetization reversal of the second pattern. Thus, the magnetic relaxation time including a value corresponding to the actual recording bit pattern can be obtained.

The above second pattern may be uniform magnetization having a constant magnetizing direction.

According to this aspect of the present invention, the whole surface of the magnetic recording medium can be uniformly magnetized in the constant magnetizing direction to form the second pattern. Thus, the second pattern can be easily formed.

The above first pattern may be formed so as to have areas of +bits and areas of −bits which both areas are arranged at a frequency based on a density to be guaranteed, the sum total of areas of +bits being equal to the sum total of areas of −bits.

According to this aspect of the present invention, the magnetic relaxation time corresponding to recording data approximate to actual recording data can be obtained. Thus, the more accurate evaluation of the record life can be obtained.

Further, the above objects of the present invention are achieved by a measurement method of a time constant of magnetization relaxation in a magnetized sample, comprising the steps of: (a) measuring remanence time response of the magnetized sample; (b) obtaining a characteristic of transient response of the remanence based on a measurement result of the remanence time response; (c) obtaining a time constant of magnetization reversal based on the characteristic of transient response of the remanence obtained in the step (b).

According to the present invention as described above, the detailed variation of the remanence can be obtained.

BRIEF DESCRIPTION OF THE DRAWINGS

Other objects, features and advantages of the present invention will be apparent from the following description when read in conjunction with the accompanying drawings, in which:

FIG. 21 is a diagram illustrating the bit record life with respect to the linear recording density which is to be evaluated in the embodiment of the present invention.

DESCRIPTION OF THE PREFERRED EMBODIMENTS

A description will be given of an embodiment of the present invention.

Figure 1:
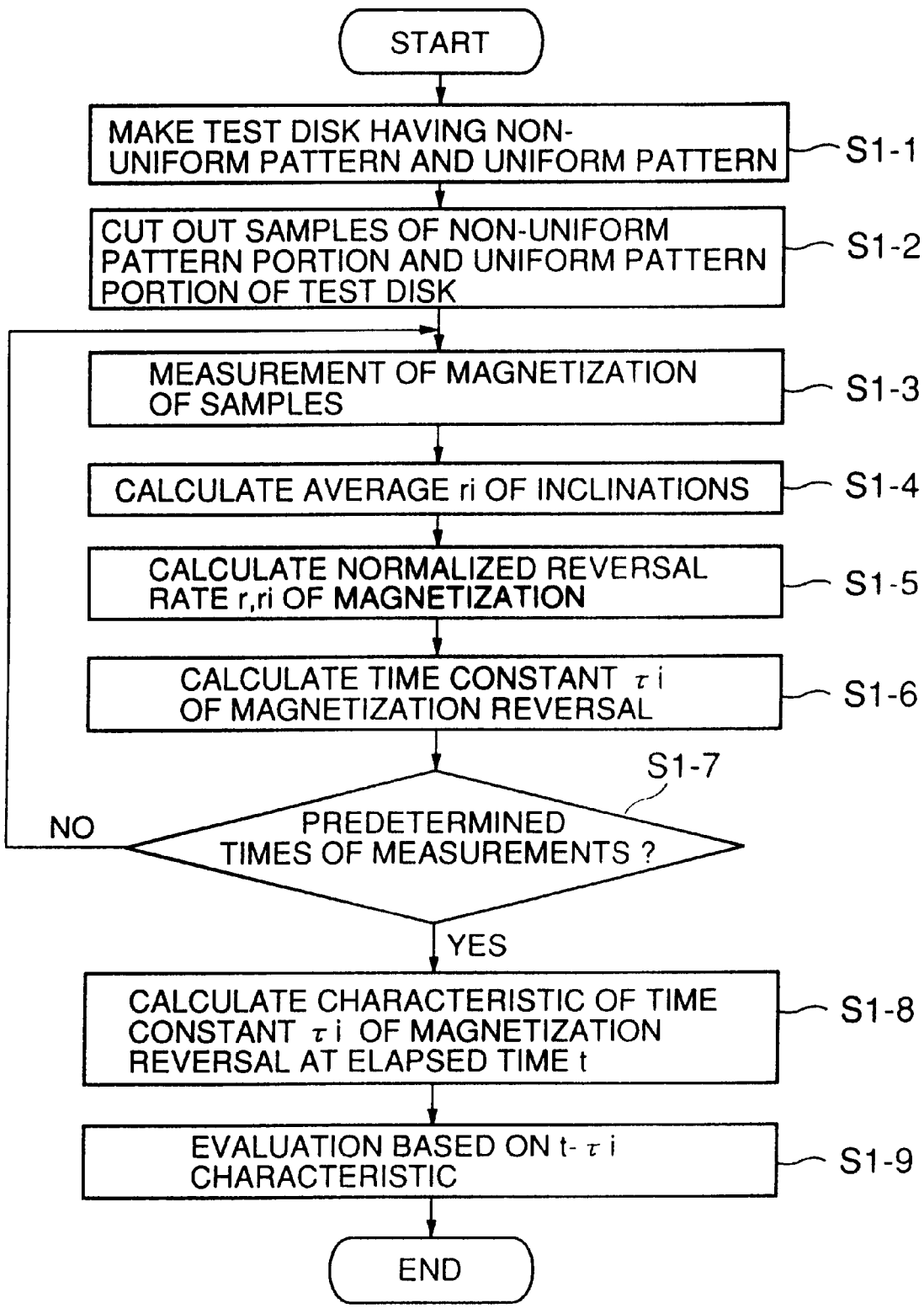
FIG. 1 is a flowchart illustrating a procedure of a method for testing a magnetic recording medium according to an embodiment of the present invention.

A procedure of testing a magnetic recording medium according to an embodiment of the present invention is formed as shown in FIG. 1.

In this embodiment, recording pattern areas which are an uniformly magnetized pattern area and a recording bit pattern area in which +bits and −bits are arranged alternately in series at a density to be measured are formed on a magnetic recording medium using a RW (Read and Write) tester. As a result, a test magnetic recording medium 1 is made (step S1-1).

Figure 2:
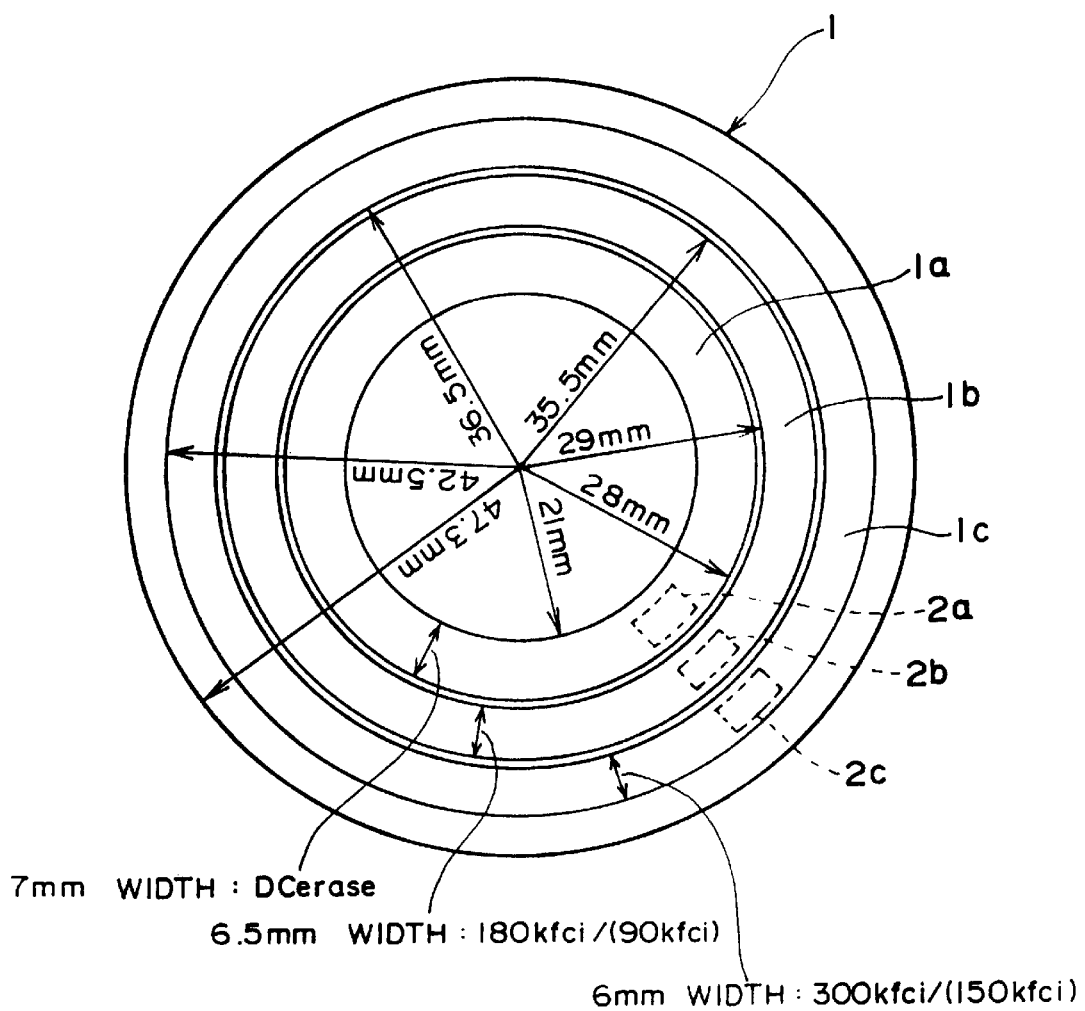
FIG. 2 is a diagram illustrating a recording format of the magnetic recording medium to be tested in accordance with the method according to the embodiment of the present invention.

A format of the test magnetic recording medium 1 made in step S1-1 is shown in FIG. 2.

The test magnetic recording medium 1 is, for example, a 3.5-inch hard disk. As shown in FIG. 2, a first recording pattern area 1a, of uniform magnetization and a width of 7 millimeters (mm), is formed between a concentric circle having a radius of 21 millimeters (mm) and a concentric circle having a radius of 28 millimeters (mm) on the magnetic recording medium 1.

In addition, a second recording pattern area 1b, having a width of 6.5 millimeters (mm), is formed between a concentric circle having the radius of 29 millimeters (mm) and a concentric circle having the radius of 35.5 millimeters (mm) on the magnetic recording medium 1. The second recording pattern area 1b is provided with +bits B1 of 90 kfci (kilo flux changes per inch; the unit of linear recording density) and −bits B2 of 180 kfci. The length of the +bits B1 differs from the length of the −bits B2 in the second recording pattern area 1b, so that the second recording pattern area 1b is not uniformly magnetized. That is, the second recording pattern area 1b is magnetized so that the residue (a half of its magnetic moment) for the +bits B1 as a result of a difference of magnetic moment between the +bits B1 and the −bits B2 appears.

Further, a third recording pattern area 1c, having a width of 6 millimeters (mm), is formed between a concentric circle having the radius of 36.5 millimeters (mm) and a concentric circle having the radius of 42.5 millimeters (mm) on the magnetic recording medium 1. The third recording pattern area 1c is provided with +bits B3 of 150 kfci and −bits B4 of 300 kfci. The length of the +bits B3 differs from the length of the −bits B4 in the third recording pattern area 1c, so that the third recording pattern area 1c is not uniformly magnetized. That is, the third recording area pattern area 1c is magnetized so that the residual magnetic moment for the +bits B3 appears.

The first, second and third recording patterns 1a, 1b and 1c are written by a read/write tester. In the first recording area 1a, uniform magnetization is formed on a plurality of tracks by a magnetic head. In the second and third recording areas 1b and 1c, the +bits B1 and B3 and the −bits B2 and B4 are alternately in series written in tracks.

Figure 3A:
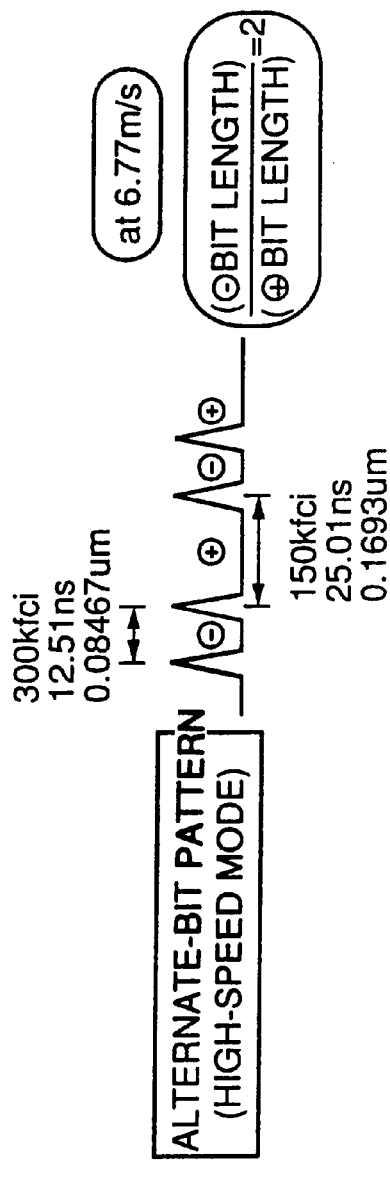
FIGS. 3A, 3B and 3C are diagrams illustrating conditions under which bits or uniform magnetization are recorded in the magnetic medium in accordance with the method according to the embodiment of the present invention.
Figure 3B:
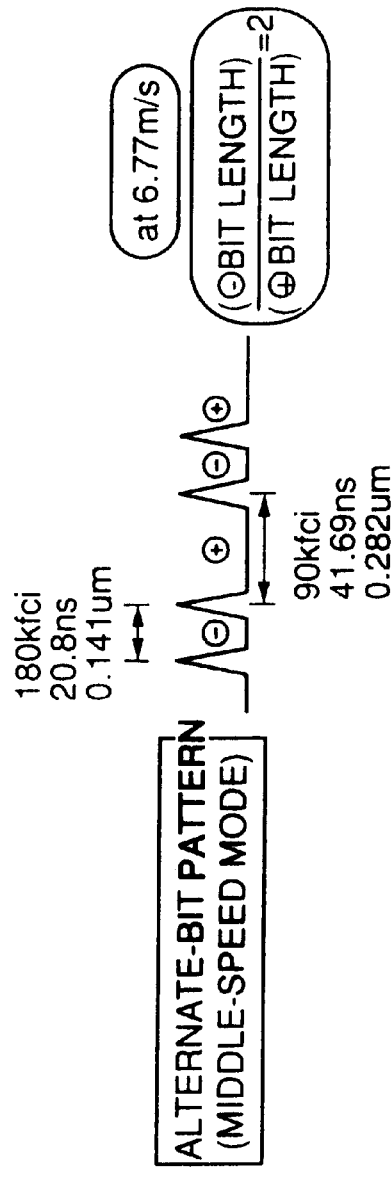
Figure 3C:
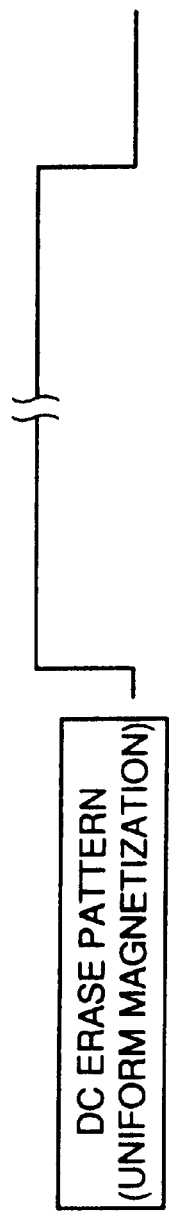

In the testing method for the magnetic recording medium according to the embodiment of the present invention, the record is performed by the RW (read/write) tester under conditions of pattern writing sequences as shown in FIGS. 3A, 3B and 3C. FIG. 3A shows a high-speed bit pattern used to form the third recording pattern area 1c. FIG. 3B shows a bit pattern to form the second recording pattern area 1b in a middle-speed mode. FIG. 3C shows a uniform magnetizing pattern used to form the first recording pattern area 1a.

The RW tester has a high flux-density type head in which a gap width of 4.5 micrometers ($\mu$m) is formed. To form the third recording pattern area 1c, the head is controlled at the spacing of 50 nanometers (nm), the circumferential speed of 6.77 meters/second (m/s) and the recording current of 40 milliamperes (mA) and the RW tester carries out a recording operation under a condition shown in FIG. 3A.

In addition, to form the second recording pattern area 1b, the high flux-density type head is controlled in the same manner as in the above case and the RW tester carries out the recording operation under a condition shown in FIG. 3B.

Figure 4A:
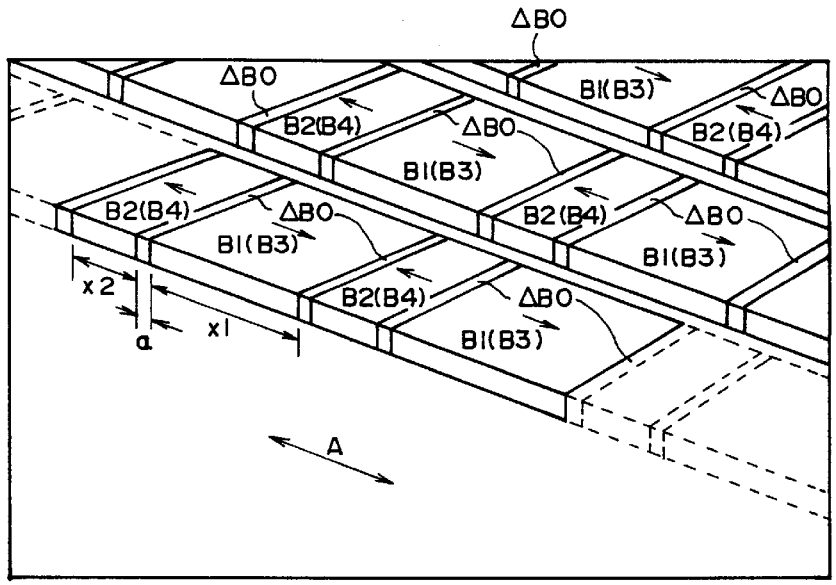
FIGS. 4A and 4B are diagrams illustrating bit patterns formed on the magnetic recording medium to be tested in accordance with the method according to the embodiment of the present invention.
Figure 4B:
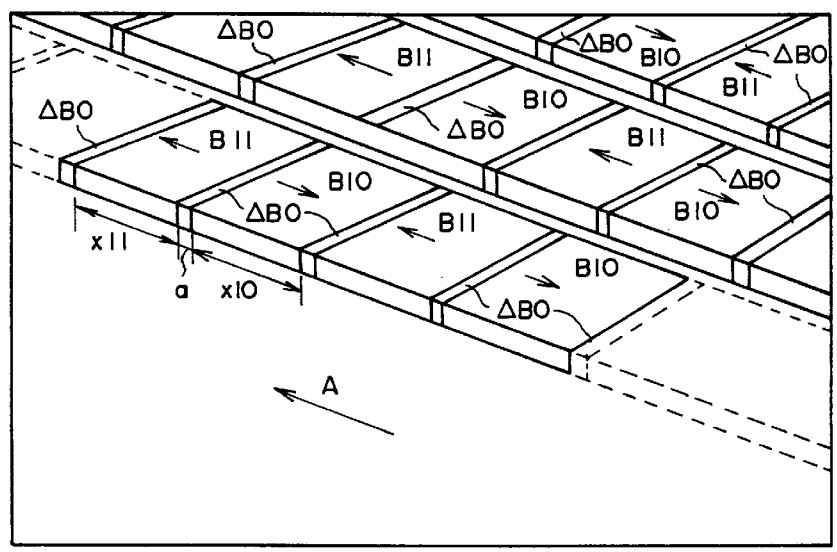

FIGS. 4A and 4B show schematically a bird's eye view of bit patterns on the test magnetic recording medium 1 used in the resting method according to the embodiment of the present invention. The second and third recording pattern areas 1b and 1c are formed as shown in FIG. 4A. FIG. 4B shows a modification of the bit pattern on the second or third recording pattern area 1b or 1c.

In a case where the second recording pattern area 1b (or the third recording area 1c) is formed by the writing operation of the read/write tester under the condition shown in FIG. 3A (or FIG. 3B), the bits B1 (or B3) and the bits B2 (or B4) are alternately arranged in series on each of a plurality of the tracks so that a transition region Δ B0 is set between a bit B1 (or B3) and a bit B2 (or B4). The length x1, in a direction A in which the tracks expand, of each of the bits B1 (or B3) is twice as large as the length x2 of each of bits B2 (or B4). The length x2 of each of the bits B2 (or B4) is half of the length x1 of each of the bits B1 (or B3).

In the second recording area 1b (or the third recording area 1c), next to a bit B1 (or B3), a different type of bit B2 (or B4) is always located. The direction of the magnetization of each of the bits B1 (or B3) is opposite to the direction of the magnetization of each of the bits B2 (or B4). The length x1 of each of the bits B1 (or B3) is greater than the length x2 of each of the bits B2 (or B4).

In the embodiment of the present invention, the first recording pattern area 1a is uniformly magnetized by the read/write tester with the DC erase mode. On the other hand, after the whole surface of the magnetic recording medium 1 is uniformly magnetized in a circumferential direction, the writing operation of the read/write tester may be carried out in only the second and third recording pattern areas 1b and 1c if the writing brings about no vacant space between the tracks.

In the second recording pattern area 1b or the third recording pattern area 1c, the length x10 of each of the bits B10 may be equal to the length x11 of each of the bits B11 as shown in FIG. 4B. In this case, the measurement can be performed under a condition in conformity with the actual bit pattern, so that the life can be more accurately evaluated.

The testing magnetic recording medium 1 may be a uniaxial anisotropy medium to which a texture process is applied in a circumferential direction or an isotropic medium to which the texture process is not applied. The bit direction and a direction of the demagnetization may be set at one of the circumferential directions.

When tracks are formed, it is ideal that there is no space between tracks. It is not preferable that tracks are overlapped, because bits are interrupted or the part of bits is overwritten. On the other hand, a slight space between adjacent tracks has no problem. The space between adjacent tracks can be roughly set.

Returning to FIG. 2, samples 2a, 2b and 2c each of which has an area of 5 mm×10 mm are cut out of the first, second and third recording pattern areas 1a, 1b and 1c of the test magnetic recording medium 1 which has been made as described above (step S1-2).

Each of the samples 2a, 2b and 2c which are cut out of the test magnetic recording medium 1a is applied with the measurement of the remanence time response (steps S1-3).

At this time, a period 1 of time elapsing from each of times at which the writing operations for the high-speed bit pattern' the middle-speed bit pattern and the uniform magnetizing pattern are performed is always recorded. In the measurement of the remanence time response in step S1-3, the SQUID is used.

Figure 5:
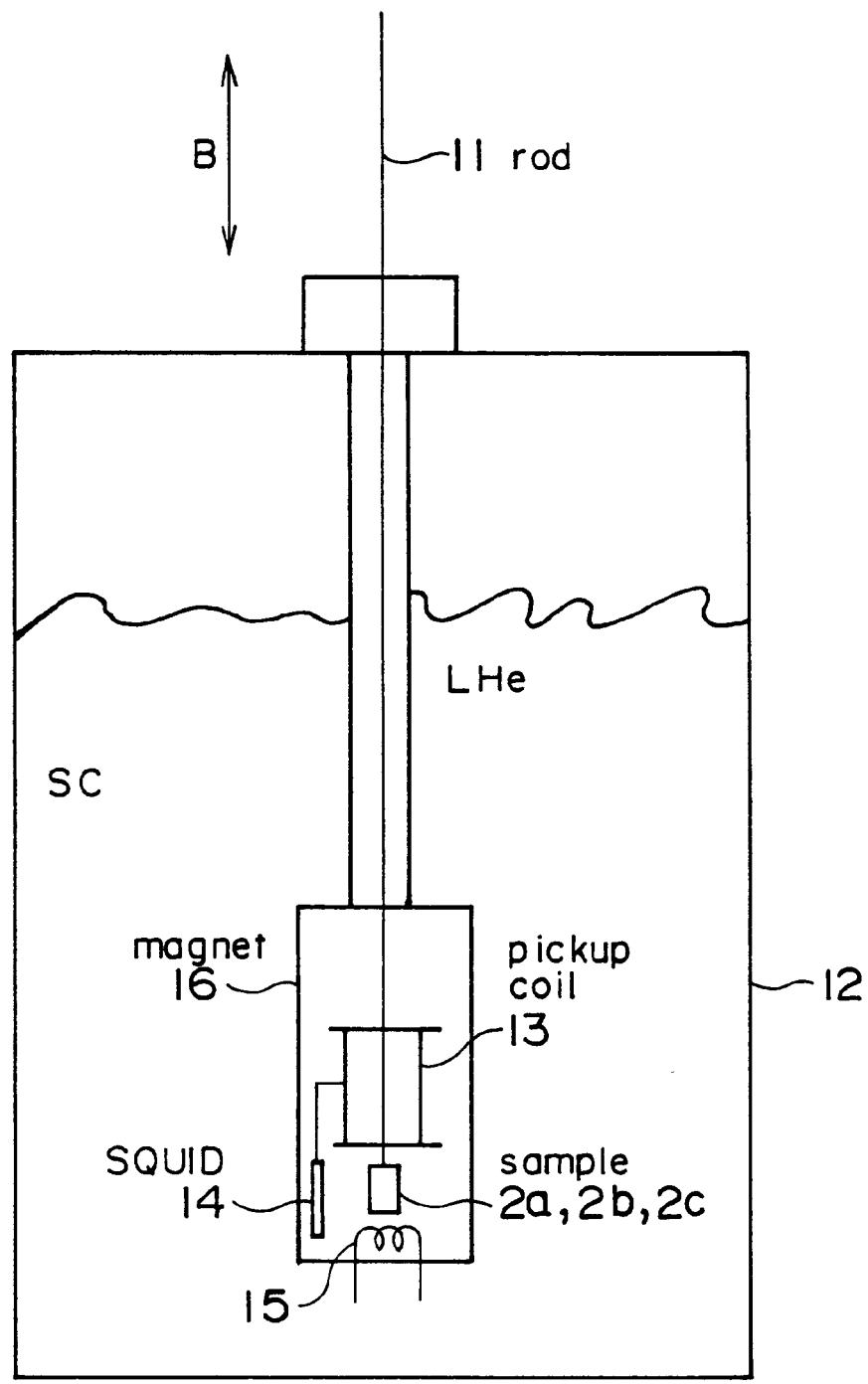
FIG. 5 is a diagram illustrating a structure of an SQUID used in the measurement of the remanence time response magnetization in the embodiment of the present invention.

The SQUID used in the testing method according to the embodiment of the present invention is formed as shown in FIG. 5.

A device 10 shown in FIG. 5 is the standard SQUID. One of the samples 2a, 2b and 2c cut out is mounted at the end of a rod 11. The sample mounted on the end of the rod 11 is set in a case 12 which is filled with liquid helium LHe.

The sample 2a, 2b or 2c set in the case 12 is reciprocated in a pick-up coil 13. Since, the sample 2a, 2b or 2c is magnetized, reciprocation of the sample 2a, 2b or 2c, causes a current to be generated in the pick-up coil 13. This operation is repeated at predetermined intervals Δ to. While the operation is repeatedly being performed, the amount of residual magnetic moment is successively measured as a transient value in the magnetic relaxation process.

The current generated in the pick-up coil 13 is detected by a SQUID unit 14 so that micromagnetization in the sample 2a, 2b or 2c is detected. In this case, the sample 2a, 2b or 2c is heated by a heater 15 so as to be maintained at a room temperature. Further, the pick-up coil 13 and the SQUID unit 14 are covered with an SC magnet 16 and shield from the external magnetic field.

After starting the measurement, the amount of residual magnetic moment is repeatedly measured at intervals ($\Delta t_o$) of about 2 minutes for time equal to or greater than a few hours. After the measurement is completed, the same measurement is executed again at a different period of time.

As to the samples 2a, 2b and 2c, a single sample is cut out of each of the recording pattern areas 1a, 1b and 1c. The sample has the size which can be set in the SQUID 10 and is sufficient to detect the residual magnetic moment with a proper sensitivity.

In the present embodiment, the SQUID 10 is used to measure the residual magnetic moment of the samples 2a, 2b and 2c. However, the present invention is not limited to this, another type of device may be used to measure the residual magnetic moment of the samples.

Based on the characteristic of the amounts of measured residual magnetization with the passage of time, the average of inclinations each of which is provided between a measured value at each measurement time point and a measured value at another measurement time point is calculated (step S1-4).

A description will be given of the process in step S1-4.

Figure 6:
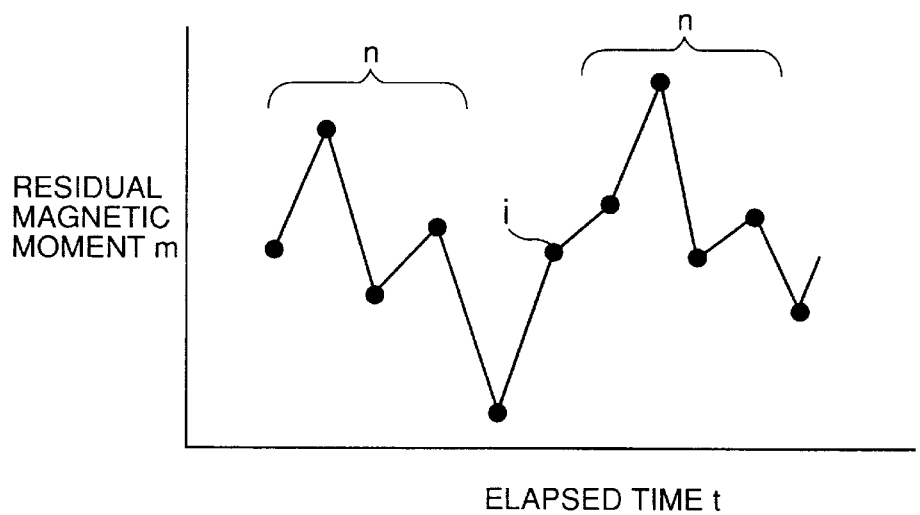
FIG. 6 is a conceptual sketch illustrating the remanence time response obtained by the method according to the embodiment of the present invention.

FIG. 6 shows a conceptional sketch of the measurement of the residual magnetic moment.

Measured values at sequentially measurement time points are fluctuated as indicated by a continuous line in FIG. 6. In the conventional case, the measured values are continuously obtained for a long time, a sample formed of inclinations is drawn out of a whole group of the measured values at the respective time points. Based on the obtained inclinations, the magnetic relaxation time is estimated.

On the other hand, in the present embodiment, a measurement point i defined by a measured value mi and a measurement time point ti is noted. A group of (2n+1) measurement points including the noted measurement point i, n measurement points obtained before the measurement time point ti and n measurement points obtained after the measurement time point ti are then provided.

Figure 7:
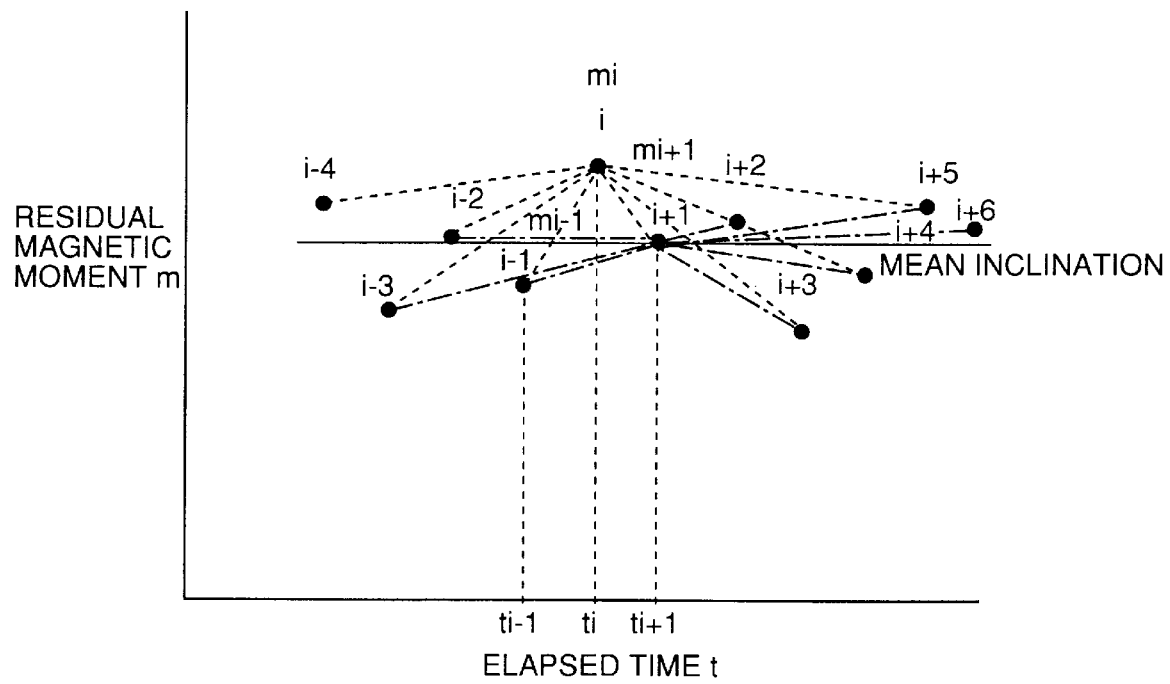
FIG. 7 is a schematic diagram illustrating a method for processing the measurement result of the remanence response.

FIG. 7 illustrates a schematic diagram of a method of processing the results of measurement of the residual magnetic moment.

First, the transient tendency of the magnetic relaxation indicated by a group of the measurement points is obtained. An averaging process using the least square method is applied to a group of (2n+1) measurement points so that the inclination as shown by a continuous line in FIG. 7 is obtained by means of the linear approximation. The inclination of the continuous line shown in FIG. 7 is obtained by averaging inclinations, using the least square method, each of which inclinations is provided between a measuring point i and one of other measurement points (i−1) through (i−4), and (i+1) through (i+4) as shown by a dashed line. The obtained inclination is given as an inclination $r_i$ at the measurement time $t_i$.

The same operations are applied to the respective measurement points, so that data items r(i) ( . . . , $r_{i-1}$, $r_i$, $r_{i+1}$, . . . ) regarding the inclinations at time points t(i) ($t_{i-1}$, $t_i$, $t_{i+1}$. are obtained.

In the above operations, if measurement points corresponding to noises are obtained, the measurement points are eliminated.

The number n defining the number (2n+1) of measurement points used to detect the tendency of the magnetic relaxation is decided as follows.

The number n is successively decremented from the maximum number corresponding to all the measurement points until immediately before values of adjacent data items, each of which is calculated from the number (2n+1) of measurement points, slightly differ from each other (the difference between the data items $r_i$ and $r_{i-1}$ is significant). The final number is then defined as the upper limit of an allowable range. On the other hand, the number n is incremented one by one from one. When the variation of the data items, each of which is calculated from the number (2n+1) of measurement points, becomes small (the difference between the data items $r_i$ and $r_{i-1}$ is small), the number n is defined as the lower limit of the allowable range.

After the upper and lower limits of the allowable range are decided as described above, a proper number n is selected from the allowable range. Although it is not necessary to strictly decide the number (2n+1) of measurement points, it is preferable that the number (2n+1) of measurement points falls within a range between 5 and 100 although the range depends on the measurement interval $\Delta t_o$.

$$5<(2n+1)<100$$

The above situation may be represented by using a measurement period of time corresponding to the allowable range of the number (2n+1). In this case, although it is not necessary to strictly decide the allowable range of successive time points corresponding to the (2n+1), the allowable range of successive time points may be not less than 5 minutes and not greater than one hour. The time points t(i) ( . . . , $t_{i-1}$, $t_i$, $t_{i+1}$, . . . ) are selected from the allowable range of successive time points and corresponding (2n+1) measurement points are then selected. In general, this type of measurement is continuously carried out for a period of time which is not less than a few hours. Thus, in the present embodiment, the number (2n+1) of measurement points used to detect the transient tendency of the magnetic relaxation is greatly smaller than the number of all the measurement points.

$$(2n+1)<<(\text{the number of all the measurement points})$$

Next, returning to FIG. 1, to normalize the data items, each of the data items r(i) ( . . . , $r_{i-1}$, $r_i$, $r_{i+1}$, . . . ) is divided by a corresponding one of the measured values m(i) ( . . . , $m_{i-1}$, $m_i$, $m_{i+1}$, . . . ) (step S1-5).

The normalized data items are represented by rr(i) ( . . . , $rr_{i-1}$, $rr_i$, $rr_{i+1}$, . . . ). The normalized data items rr(i) are referred to as a normalized sequential rate of magnetization reversal.

An inverse number of the normalized sequential rate of magnetization reversal is then calculated (step S1-6). The inverse number of the normalized sequential rate of magnetization reversal calculated in step S1-6 is the sequential time constant of magnetization reversal and represented by data items τ(i) ( . . . , $\tau_{i-1}$, $\tau_i$, $\tau_{i+1}$, . . . ).

During the measurement, data times r(i) may be inverted from a positive value to a negative value and vice versa. When a data item has the negative value, the absolute value of the data item is calculated and information of the negative value is added. Absolute values of the data items rr(i) and τ(i) corresponding to the data items r(i) are calculated.

Although, finally, all the data items have positive values, data items calculated from the data items having positive values are referred to as positive data items, and data items calculated from the data items having negative values are referred to as negative data items. The negative data items are named demagnetizing data items and the positive data items are named magnetizing data items.

At different period of times after the writing operation is completed, the process from step S1-3 through S1-6 is repeatedly executed. At each period, the time constant $\tau_i$ of magnetization reversal is calculated (step S1-7).

The various types of data items r(i), rr(i) and $\tau(i)$ based on the results of the measurement on the period marked j of the elapsed time are represented by $r(i)_j$, $rr(i)_j$ and $\tau(i)_j$.

Next, the sequential time constant $\tau(i)$ of magnetization reversal is assigned to the axis of coordinates and the elapsed time t is assigned to the axis of abscissas. Data items $\tau(i)_{jj-1}$, $\tau(i)_j$, $\tau(i)_{j+1}$, ... on a series of period marked j−1, j, j+1, ... are plotted. As a result, the characteristic of the time constant of magnetization reversal with respect to the elapsed time is obtained (step S1-8).

Based on the characteristic of the time constant of magnetization reversal with respect to the elapsed time obtained in step S1-8, various kinds of evaluation are carried out (Sl-9).

A description will now be given of the evaluation method based on the characteristic obtained in step S1-8.

In a case where the length x1 of each bit B1 (or B3) is greater than the length x2 of each bit B2 (or B4) (x1>x2), based on the positive data items r(i), rr(i) and $\tau(i)$, the magnetic relaxation information of magnetic particles in short bits B2 (or B4) is extracted. From the negative data items, the magnetic relaxation information of magnetic particles in long bits B1 (or B3) is extracted.

In addition, in a case where the length x1 of each bit B1 (or B3) is equal to the length x2 of each bit B2 (or B4) (x1=x2), the magnetic relaxation information of magnetic particles in bits are extracted from both the positive and negative data items.

Values of the time constant of magnetization reversal measured on a different time j are plotted on a graph, and the plotted points are extrapolated and interpolated. As a result, the tendency of change in a long term is obtained. Based on this tendency, the bit record life can be evaluated.

In a case that the characteristic obtained in step S1-8 indicates a monotonously decreasing characteristic as a general long-term tendency, the plotted points on the characteristic obtained in step S1-8 are extrapolated in accordance with the extrapolation method in an increasing direction of the elapsed time, so that an elapsed time point corresponding to the time constant of magnetization reversal of 100 seconds is obtained. The time constant of magnetization reversal of 100 seconds characterizes the paramagnetism.

To evaluate the bit record life, the method of evaluating the relaxation characteristic with respect to the logarithmic scale of time based on the measurement of the relaxation of the uniform magnetizing pattern is used. Moreover, the magnetizing pattern which is not uniform is characterized by a reduction rate s. The relaxation characteristic with respect to the logarithmic scale of time based on the measurement of the relaxation of the uniform magnetizing pattern is multiplied by the reduction rates so that the evaluation is carried out.

A description will now be given of the evaluation method of the bit record life.

In this embodiment, as to the time constant of magnetization reversal regarding the magnetic relaxation due to the thermal fluctuation, a rate of a value in a case of a bit pattern to a value in a case of the uniform magnetization is calculated. Since this rate is less than one in a case of a high linear recording density bit pattern, this rate is named the reduction rate.

The reduction rate s is defined as follows.

$$s = A/B \quad (1)$$

A: a value of reversal time constant of a bit pattern

B: a value of reversal time constant of uniform magnetization

In a conventional case, based on a value of the so called % demagnetization or % fall off of magnetization during time progress, the record life regarding the magnetic relaxation due to the thermal fluctuation is quantitatively evaluated. The % demagnetization is obtained by the extrapolation of the relaxation characteristic, regarding the magnetic relaxation of the uniform magnetization due to on the thermal fluctuation, with respect to the logarithmic scale of time.

First, the measurements for the bit pattern and the uniform magnetization are carried out. The respective data items $\tau(i)_j$ which are based on the same period marked j or data items $\tau(i)_j$ and $\tau(i)_{j+1}$ which are based on periods close to each other are supplied to the above equation (1) so that a value of the reduction rate s is obtained.

Next, from the relaxation characteristic with respect to the logarithmic scale of time regarding the uniform magnetization, a period of time range for magnetic relaxation due to the thermal fluctuation regarding the % demagnetization is obtained. For example, when a case where the demagnetization from an initial magnetization is 10% is selected, this time range for % demagnetization is defined as t (10%). Finally, a time range required for 10% demagnetization of the bit pattern which should be evaluated is evaluated as follows.

$$s \cdot t(10\%) \quad (2)$$

This formula gives the bit record life for 10% demagnetization. In the same manner, a time range required for x % demagnetization is evaluated as follows.

$$s \cdot t(x\ \%) \quad (3)$$

According to the present embodiment, when the sequential time response measurement of the remanence of the bit pattern is carried out, the length of +bits and the length of −bits differs from each other (x1>x2). As a result, the sequential magnetic relaxation characteristic (the time constant of the magnetization reversal of magnetic particles in the bits) which is characterized by the linear recording densities of x1 and x2 can be obtained.

In other words, due to the limitation to the bit format defined by two types of amounts of magnetization and two types of magnetizing directions, the magnetic relaxation characteristic can be extracted as material parameters regarding magnetic particles in the respective bits from the transient response characteristic of the remanence.

In addition, under a condition in which x1 is greater than x2 (x1>x2), the collective residual magnetization can be steadily measured.

In a case of the bit format under a condition in which x1 is equal to x2 (x1=x2), the data of the linear recording density can be accurately obtained. In this case, although the collective remanence is measured as a value close to zero steadily, the data items as described above can be obtained by using pertinently substitute of m(i) the amount of the remanence obtained in a case of the uniform magnetization. Further, due to adding the uniform magnetization pattern to patterns to be used, the difference between the time constants of magnetization reversal in magnetic particles having the different magnetization patterns in the same structure, can be extracted.

Based on the (2n+1) measurement points in which the measurement point i is located at their center, the inclination ($r_i$) is calculated. Thus, in a case where the measurement value varies in accordance with a monotonous relaxation curve with statistical fluctuation, the inclination ($r_i$) line can be close to a tangential line of the curve by using the upper limit of the number n.

In addition, in a case where the measurement value varies in accordance with a rippled relaxation curve accompanied the statistical fluctuation, the number n can be close to a value of a period of the ripple.

Due to the lower limit of the number n, the inclination $r_i$ can be selected as the rate of the magnetization reversal which is peculiar to the magnetic particles without depending on the magnetization reversal in the magnetic particles which reflects the statistical fluctuation. The time constant of magnetization reversal of the particles, based on the inclination $r_i$, can be then obtained.

Further, since the sizes of particles in the magnetic recording medium are distributed, the time constant characterizing the magnetization reversal of each particle is dispersed. Thus, it is preferable that the measurement of the magnetic relaxation due to the thermal fluctuation should be repeatedly carried out at different times. As a result, the tendency of the variation of the time constant of magnetization reversal for a long period time can be definitely shown.

In addition, the relaxation characteristic formed of a group of measurement points is obtained by the measurement of the magnetic patterns of two types of bits. From this relaxation characteristic, the time constant of magnetization reversal of each magnetic particle characterized by a bit can be successively obtained.

For example, the positive data items are mainly concerned with the magnetic relaxation of the bits B2 (or B4) having the short length, and the negative data items are mainly concerned with the magnetic relaxation of the bits B1 (or B3) having the long length. If the length of the +bit and the length of the –bit are equal to each other, the values of the positive data items and the values of the negative data items are equal to each other in principle.

As has been described above, the reversal time constant of magnetic particles forming the bits can be further accurately detected. In a case where the magnetic particles have various anisotropy energies, the process of the magnetic relaxation is complex.

Thus, the measurement of the remanence and the calculation of the magnetic relaxation due to the thermal fluctuation of bits are not carried out only immediately after the bit patterns are magnetically recorded, the measurement is repeatedly carried out at different times so that the tendency of the variation of the magnetic relaxation with passage of time is obtained.

The tendency of the variation of the time constant of magnetization reversal of magnetic particles in bits for a long period of time can be definitely shown by using the extrapolation method and the interpolation method.

The time constant of magnetization reversal obtained in the present embodiment does not mean the bit record life. This is a value regarding the magnetic relaxation due to the thermal fluctuation of the magnetic particles in the bits.

Thus, in the present embodiment, the reduction rate is defined. The time constant of magnetization reversal of the magnetic particles is coupled to the bit record life by the reduction rate. This is based on the reason that the time constant of magnetization reversal regarding the magnetic relaxation due to the thermal fluctuation in the case of the bit pattern is shorter than the time constant of magnetization reversal in the case of the uniform magnetization.

It may be common understanding theoretically to think that this reduction is caused by the demagnetizing field. Although the effect of the demagnetizing field has been confirmed by using the simulation, there is almost no matter regarding actual medium. By using the reduction rate, the record life of bits having a high linear recording density which may be strongly affected by the demagnetizing field can be quantitatively evaluated.

The time constant of magnetization reversal as described above depends on only magnetic particles in which the initial magnetizing direction is initially reversed, but does not depend on magnetic particles in which the reversed magnetizing direction is returned to the initial magnetizing direction. In addition, it is determined that, at each measurement time point $t_j$, the magnetization reversal in magnetic particles of one of two types of bits is superior to the magnetization reversal in magnetic particles of another type of bits. As a result, it is neglected that the magnetization reversal of another type of bits may be interrupted during the process of magnetization reversal of one type of bits.

As indicated by the formula (3), the data obtained from the relaxation characteristic with respect to the logarithmic scale of time based on the measurement of the uniform magnetization pattern is coupled to the basic data obtained by the measurement using the reduction rate. Thus, the return of the magnetic particles to the initial magnetizing direction and the intermission of the magnetization reversal are substantially taken into account in the calculation on the bit pattern. As a result, the bit record life can be accurately obtained.

A description will now be given of the method of calculate the inclination from (2n+1) measurement points, having the measurement point i located at the center, based on examples of the actual measurement.

The magnetic recording medium used for the test is a 3.5-inch medium and has an internal structure in which a protection film, a magnetic film, an underlying film, a plating film and a base are arranged in this order from an upper surface.

The protecting film is made of DLC (Diamond Like Carbon). The magnetic film is made of CoCrPtTa. The underlayer is made of Cr. The plating film is made of NiP. The base is made of Al—Mg.

The thickness of the protecting film is 12 nanometers (nm). The thickness of the magnetic film is 10 nanometers (nm). The thickness of the underlayer is 25 nanometers (nm). The texture process is applied to the magnetic recording medium in the circumferential direction. The magnetic recording medium having the above structure has the following static magnetic characteristics.

Figure 8:
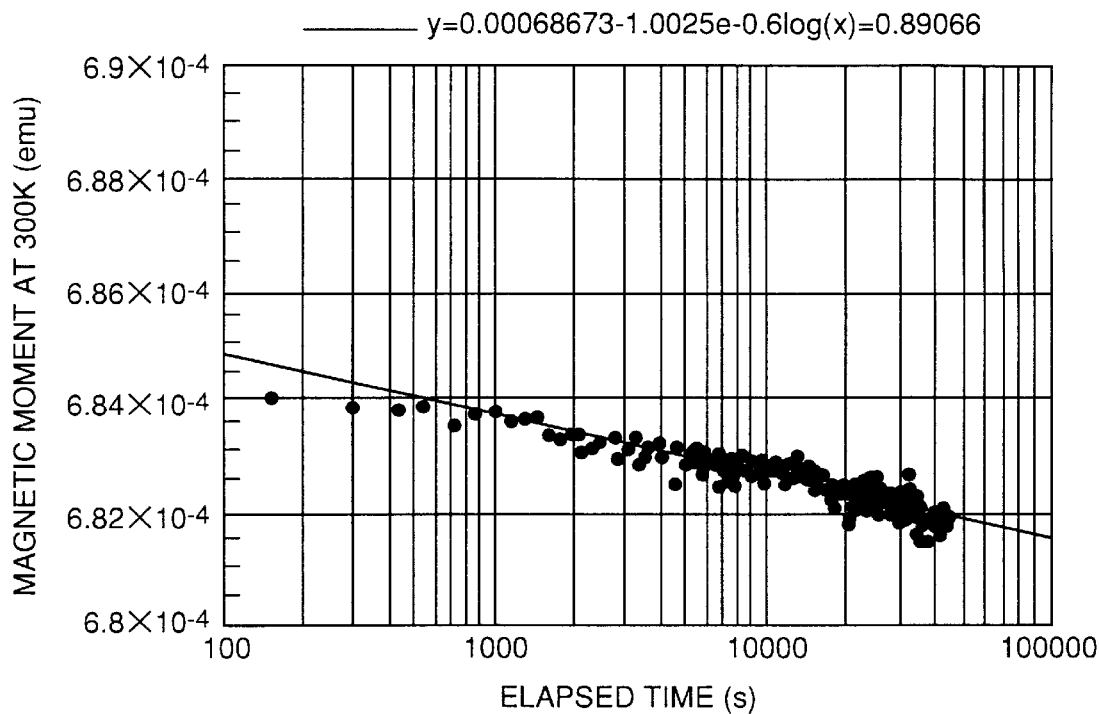
FIG. 8 is a diagram illustrating an example of the characteristic of the transient response of the remanence in the uniform magnetization pattern in the embodiment of the present invention.

$Ms=560[emu/cc]$ $Mr=425[emu/cc]$ $S=0.75$ $S*=0.73$ $Hc=1750[Oe]$ $tBr=53[Gpm]$ FIG. 8 indicates an example of the transient response characteristic of remanence of the uniform magnetization.

Referring to FIG. 8, each plotted point is a measurement point. A continuous line is a regression curve indicating the tendency of the relaxation that all the measurement points show so that the tendency of the relaxation is approximated by the relaxation with respect to the logarithmic scale of time.

The regression curve has the inclination of $1.0025 \times 10^{-6}$. In FIG. 8, values of the measurement points are not smoothly decreased. The values of the measurement points are varied with ripple. For example, the values are increased in a period between $10^4$ seconds and $1.3 \times 10^4$ seconds, decreased in a period between $1.3 \times 10^4$ seconds and $1.8 \times 10^4$ seconds and increased in a period between $1.8 \times 10^4$ seconds and $2.4 \times 10^4$ seconds.

The width of (2n+1) measurement points set as a value less than the half of the period of the ripple (the minimum value of the period of the ripple), so that the inclination $r_i$ can be obtained.

The inclination $r_i$ corresponding to a measurement point i included in the envelope having a right increased wave form has a positive value. On the other hand, the inclination $r_k$ corresponding to a measuring point k included in the envelop having a decreased-to-the-right-side wave form has a negative value. In the case of the uniform magnetization pattern, the inclination $r_k$ relates to the magnetization reversal from the initial magnetizing direction, and the inclination $r_i$ relates to the magnetization reversal to the initial magnetizing direction.

The magnetic relaxation due to the thermal fluctuation is characterized by a periodical wave form having increasing parts and decreasing parts, but on the whole by a decreasing curve which is smoothly varied with respect to the passage of time. At each time point in the relaxation, it can be determined which is superior to a phenomenon in which the magnetization is increased or a phenomenon in which the magnetization is decreased. Thus, the two phenomena can be separated on a time scale.

It is necessary to consider the following measurement condition. The random repetition of the increasing and decreasing in the relaxation process is named fluctuation. The fluctuation is caused by the small amount of statistic $(m_i - m_{i-1})$ in which the measured quantity is varied with respect to a measurement interval $(t_i - t_{i-1})$.

Thus, in the present embodiment, to consider the statistical fluctuation, the measurement is repeated at high frequency in accordance with the measured quantity (the magnetic moment in this case) which is indicated by a sample so as to be momentarily varied.

A description will be given of results.

Figure 9:
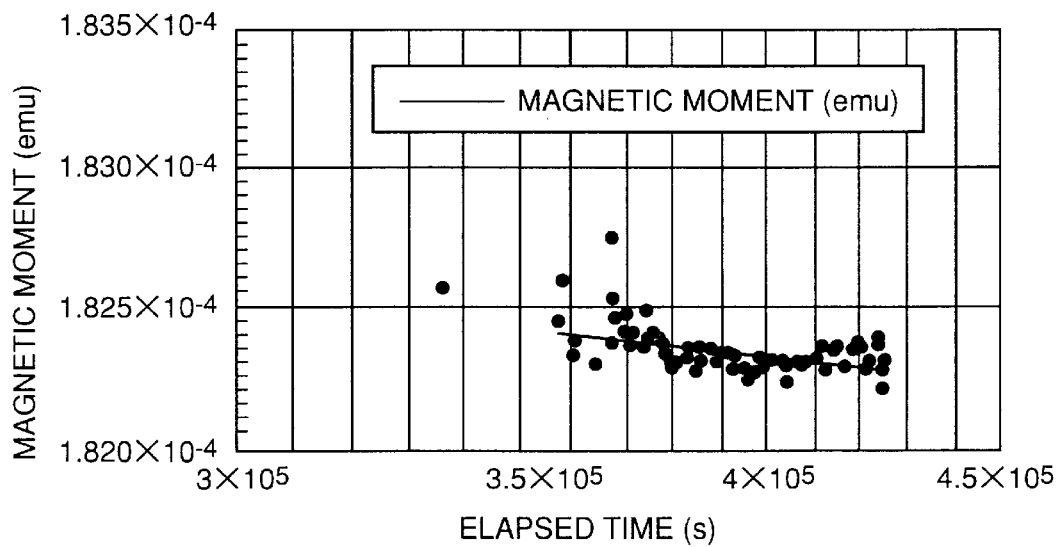
FIG. 9 is a diagram illustrating the characteristic of the transient response of the remanence in a first period of the uniform magnetization pattern in the embodiment of the present invention.
Figure 10:
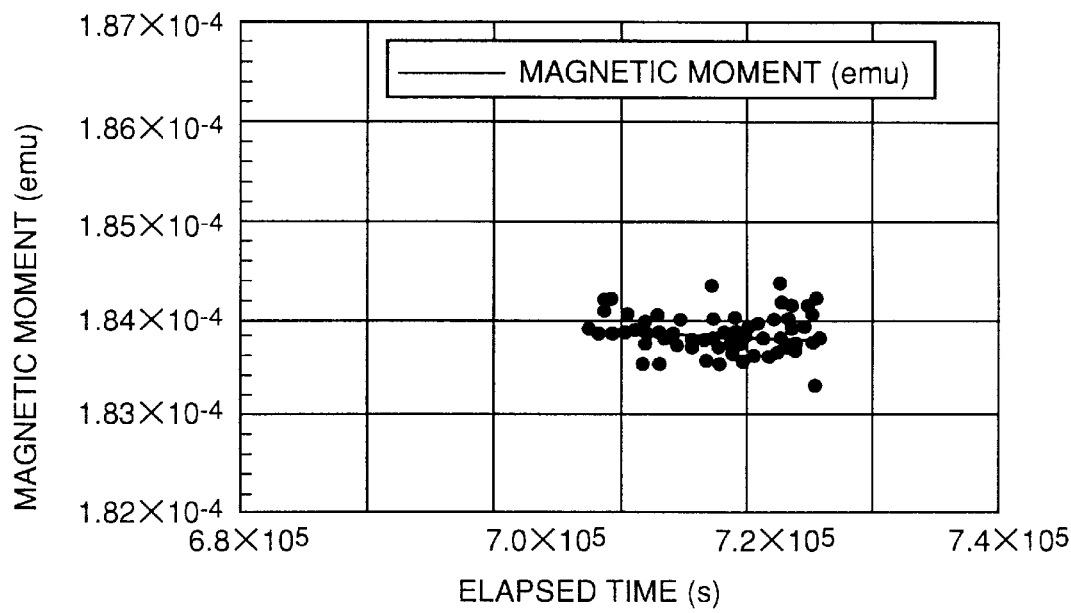
FIG. 10 is a diagram illustrating the characteristic of the transient response of the remanence in a second period of the uniform magnetization pattern in the embodiment of the present invention.
Figure 11:
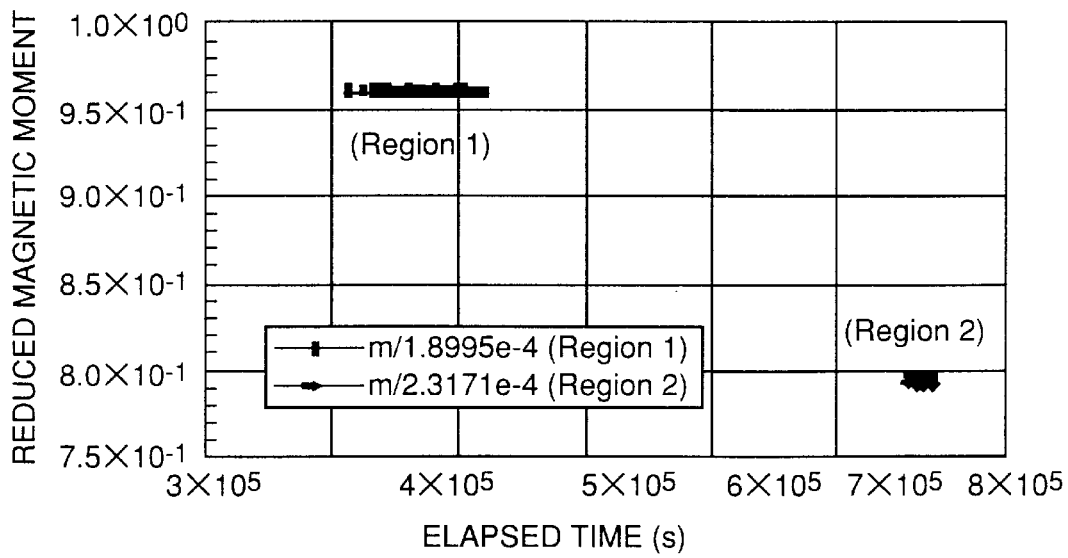
FIG. 11 is a diagram illustrating the characteristic of the transient response obtained by normalization, using an initial value, of the remanence in a period including the first and second periods of the uniform magnetization pattern in the embodiment of the present invention.

FIG. 9 shows the characteristic of the transient response of the remanence in the first period of the uniform magnetization pattern. FIG. 10 -:shows the characteristic of the transient response of the remanence in the second period of the uniform magnetization pattern. FIG. 11 is the characteristic of the transient response obtained by normalization, using an initial value, of the remanence in a period including the first and second periods of the uniform magnetization pattern.

In FIGS. 9 through 11, each of continuous lines is a regression curve for all the data points and each of indicated equations is a regression equation.

Figure 12:
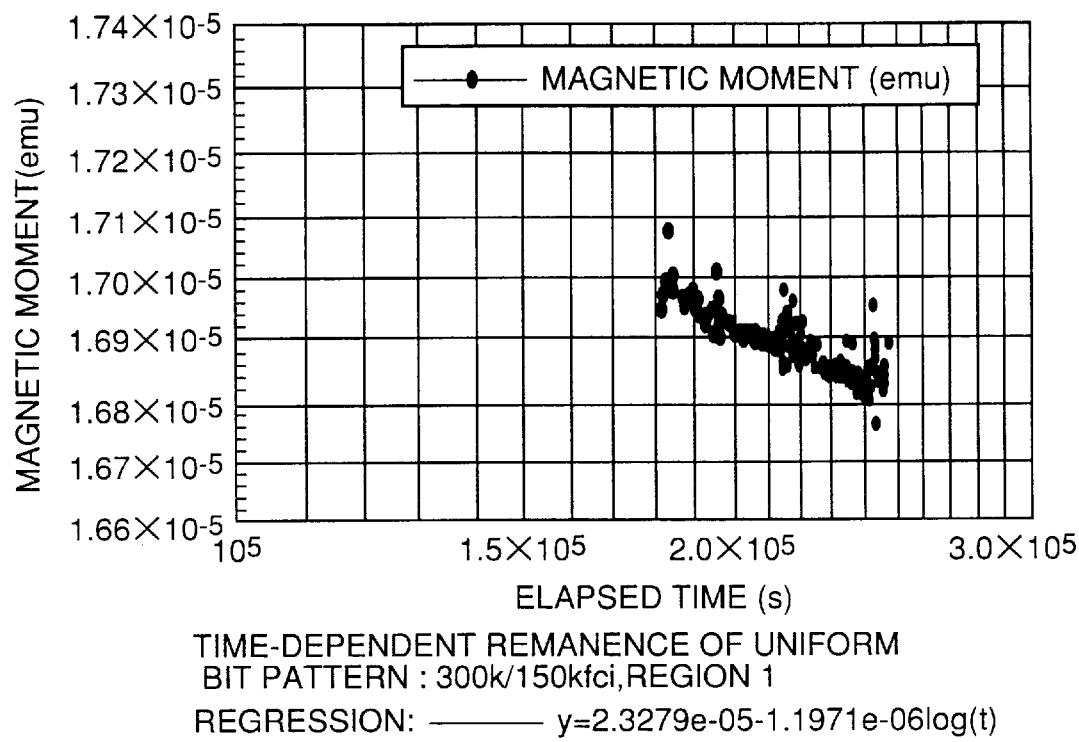
FIG. 12 is a diagram illustrating the characteristic of the transient response of the remanence in the first period of the magnetization pattern of 300/150 kfci.
Figure 13:
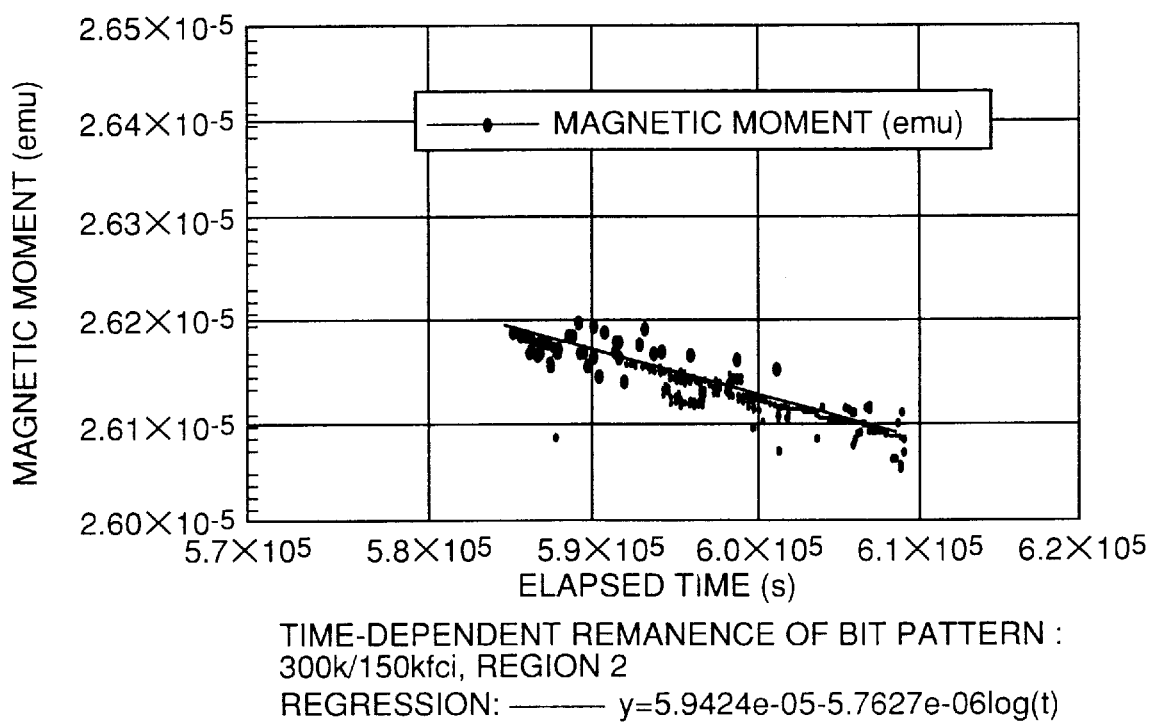
FIG. 13 is a diagram illustrating the characteristic of the transient response of the remanence in the second period of the magnetization pattern of 300/150 kfci.
Figure 14:
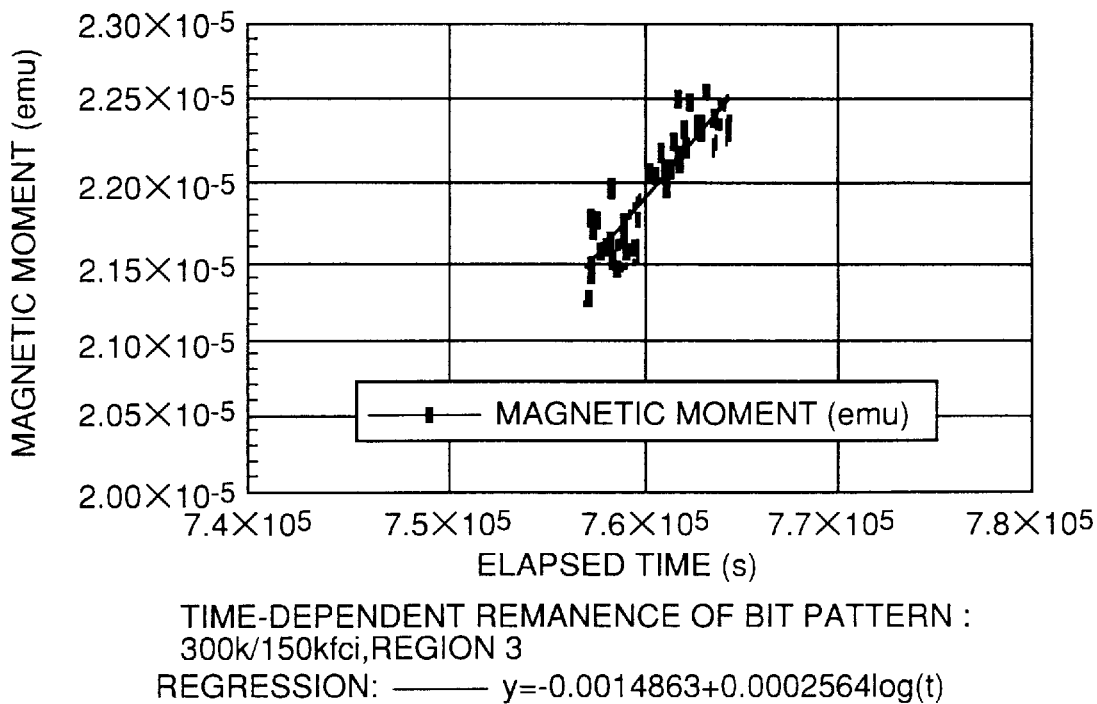
FIG. 14 is a diagram illustrating the characteristic of the transient response of the remanence in a third period of the magnetization pattern of 300/150 kfci.
Figure 15:
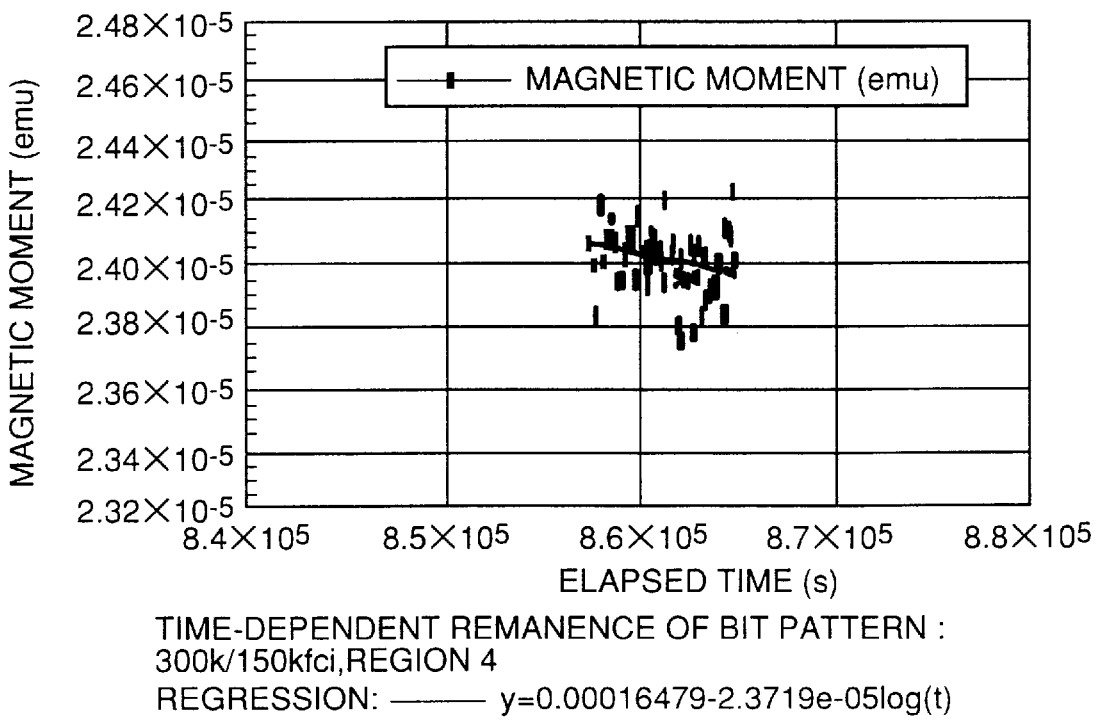
FIG. 15 is a diagram illustrating the characteristic of the transient response of the remanence in a fourth period of the magnetization pattern of 300/150 kfci.

FIG. 12 shows the characteristic of the transient response of the remanence in the first period of the magnetization pattern of 300/150 kfci. FIG. 13 shows the characteristic of the transient response of the remanence in the second period of the magnetization pattern of 300/150 kfci. FIG. 14 shows the characteristic of the transient response of the remanence in the third period of the magnetization pattern of 300/150 kfci. FIG. 15 shows the characteristic of the transient response of the remanence in the fourth period of the magnetization pattern of 300/150 kfci.

In FIGS. 12 though 15, each of continuous lines is a regression curve for all the data points and each of indicated equations is a regression equation.

For example, in each of periods shown in FIG. 12, FIG. 13 and FIG. 15, there is a tendency for the remanence to decrease with the passage of time. On the other hand, in a period (after $7.6 \times 10^5$ [s] from a time at which the writing operation is carried out) shown in FIG. 14, there is a tendency for the remanence to increase with the passage of time. There is the same tendency in a period, after $6 \times 10^5$ [s] from a time at which the writing operation is carried, of a bit pattern of 180 kfci/ 90 kfci (not shown in figure).

Figure 16:
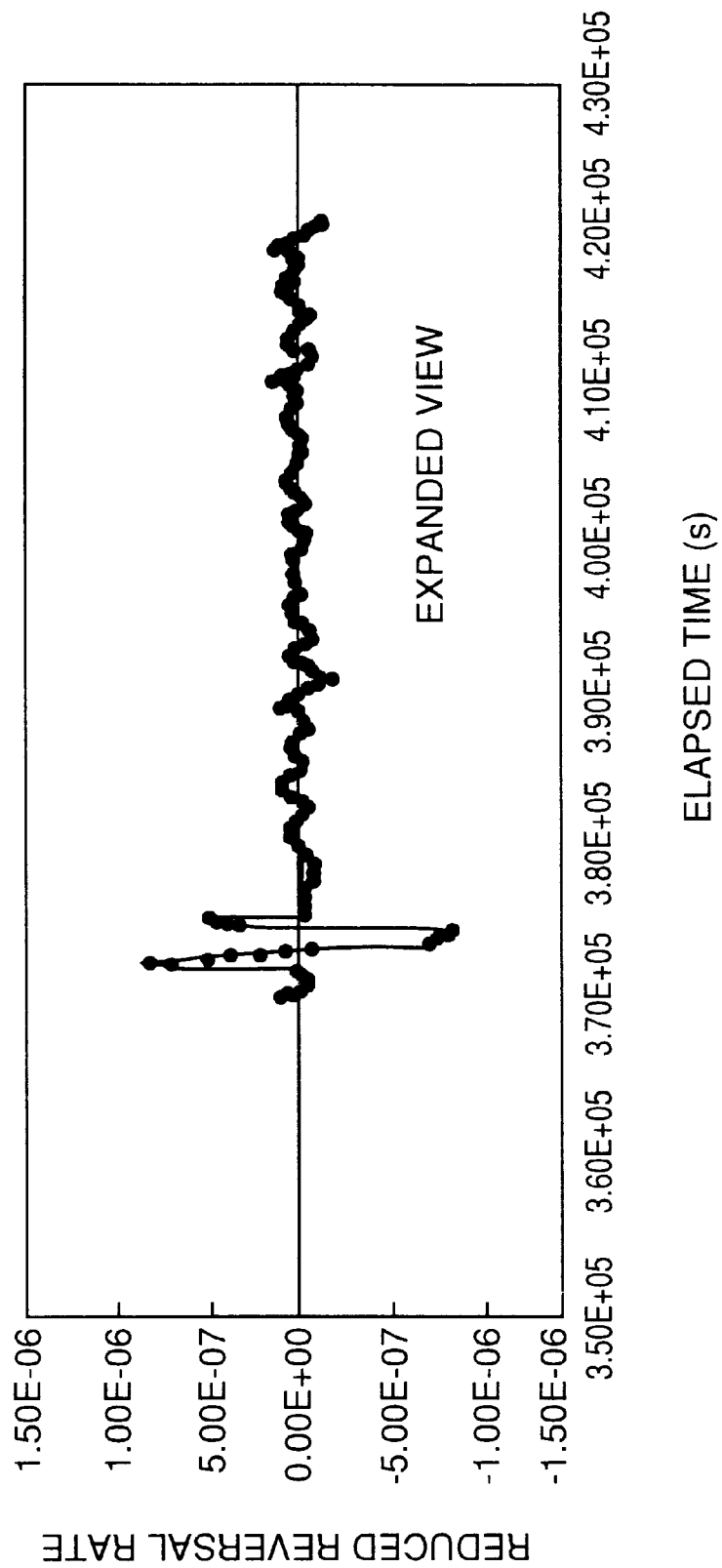
FIG. 16 is a diagram illustrating the characteristic of the normalized sequential rate of magnetization reversal with respect to the measurement time of the uniform magnetization pattern in the embodiment of the present invention.
Figure 17:
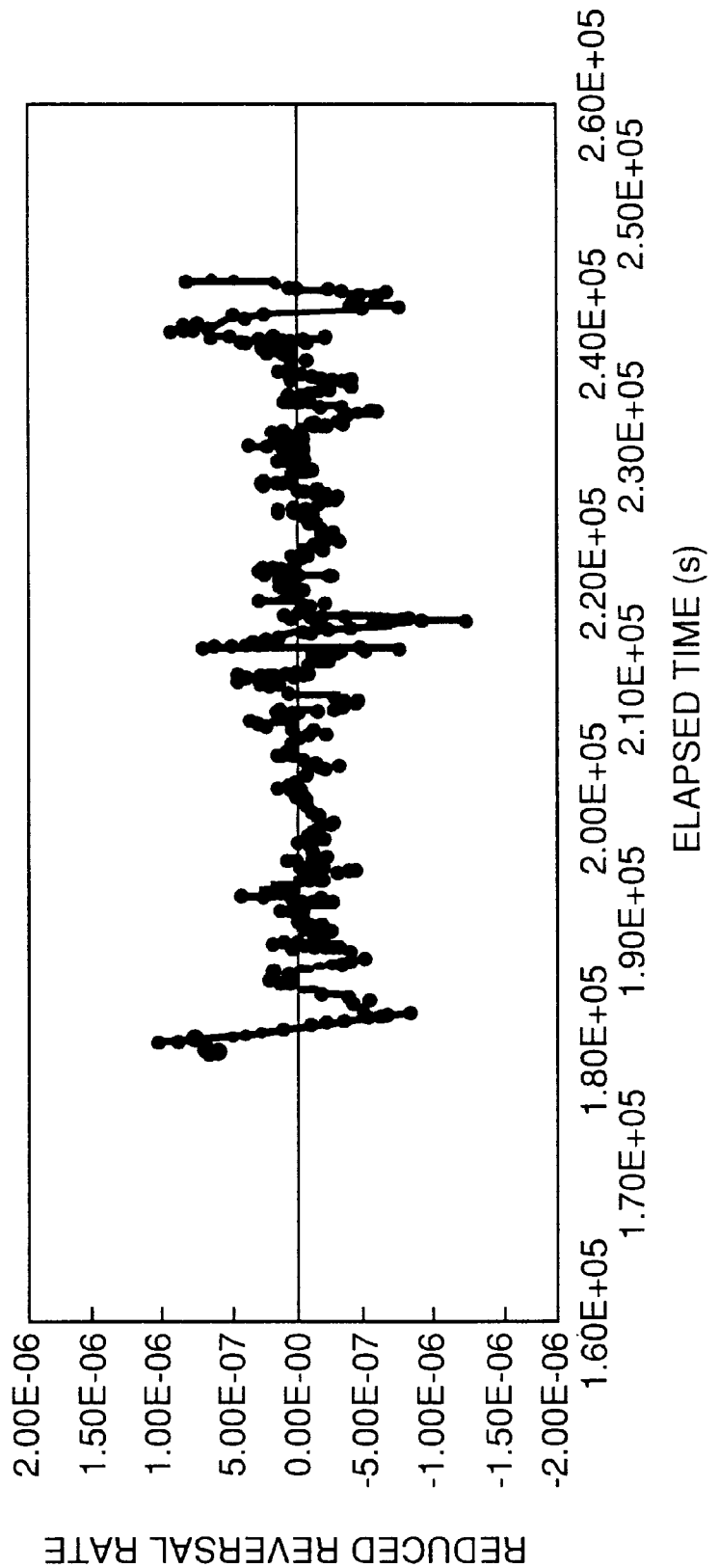
FIG. 17 is a diagram illustrating the characteristic of the normalized sequential rate of magnetization reversal with respect to the measurement time of the recorded bit pattern of 300/150 kfci in the embodiment of the present invention.

FIG. 16 shows the characteristic of the normalized sequential rate of magnetization reversal with respect to the measurement time of the uniform magnetization pattern. FIG. 17 shows the characteristic of the normalized sequential rate of magnetization reversal with respect to the measurement time of the recorded bit pattern of 300/150 kfci.

In FIGS. 16 and 17, each of continuous lines is a guide line, and each of measurement points corresponds to one of the data items rr(i) ( ...., $rr_{i-1}$, $rr_i$, $rr_{i+1}$, ... ).

The inverse number of the normalized sequential rate of magnetization reversal in the axis of coordinate as shown in FIGS. 16 and 17 is calculated, so that the time constant of magnetization reversal is obtained.

Figure 18:
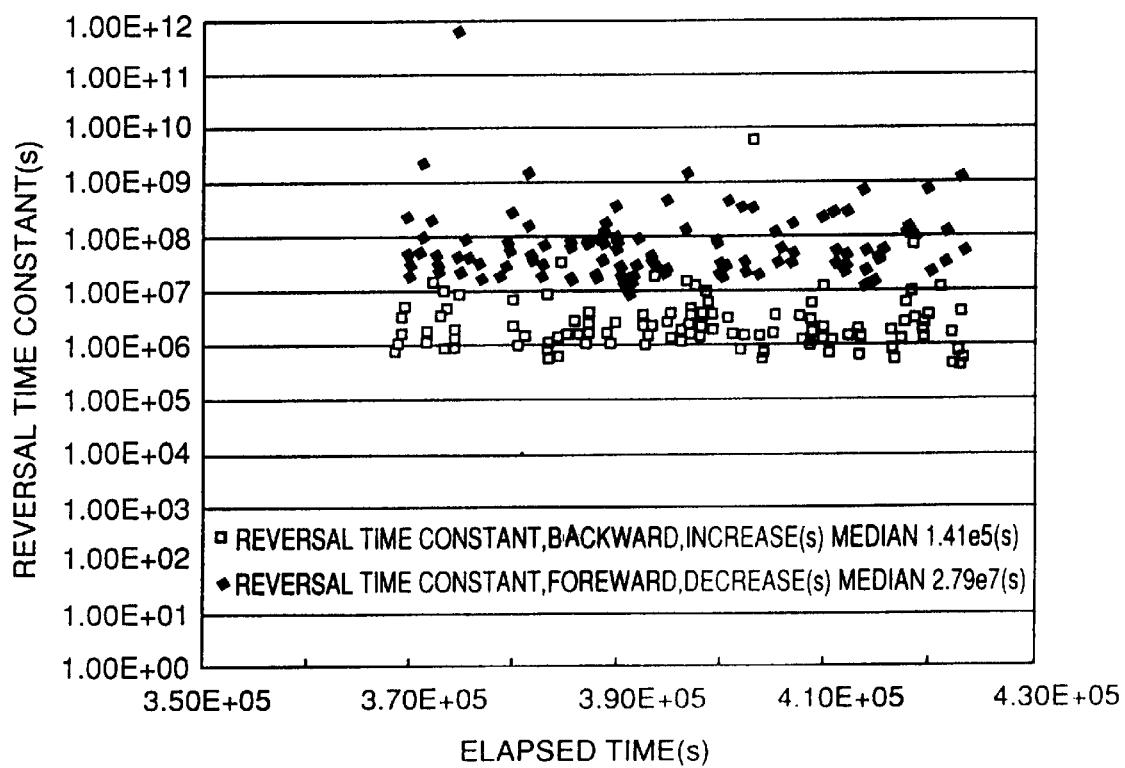
FIG. 18 is a diagram illustrating the characteristic of the time constant of magnetization reversal with respect to the measurement time of the uniform magnetization pattern in the embodiment of the present invention.
Figure 19:
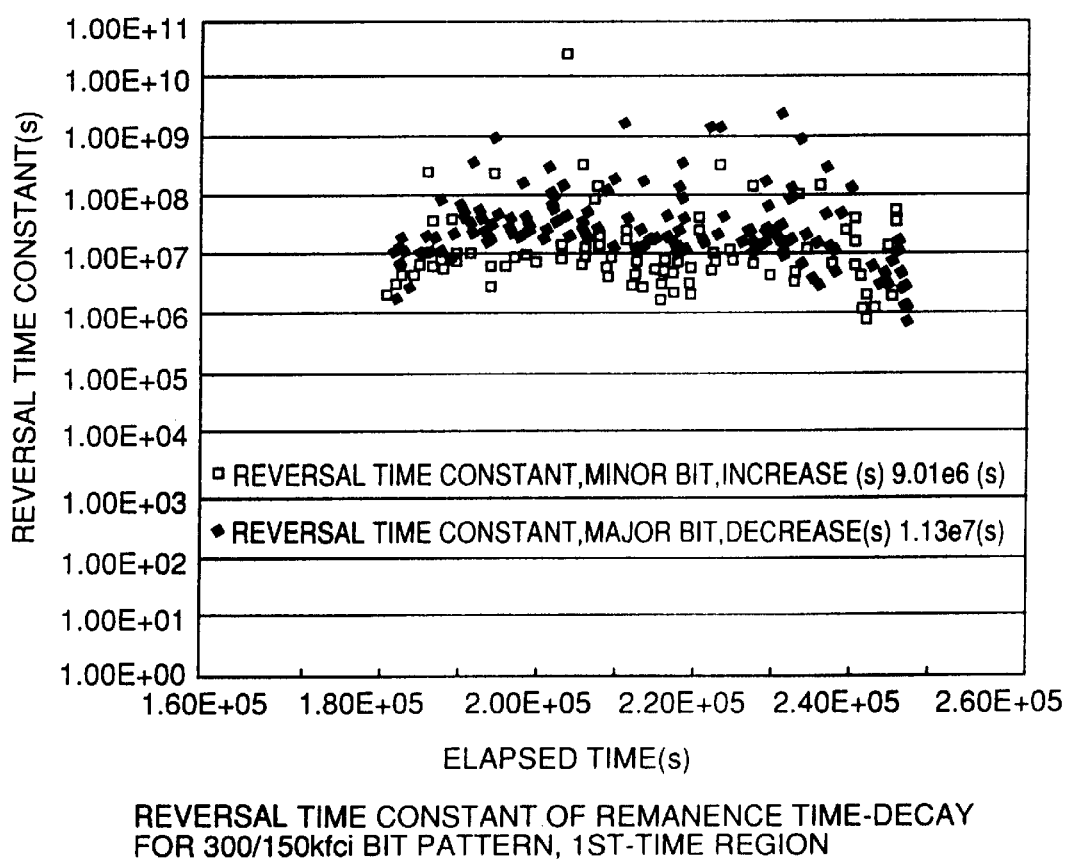
FIG. 19 is a diagram illustrating the characteristic of the time constant of magnetization reversal with respect to the measurement time of the recorded bit pattern of 300/150 kfci in the embodiment of the present invention.

In addition, FIG. 18 shows the characteristic of the time constant of magnetization reversal with respect to the measurement time of the uniform magnetization pattern. FIG. 19 shows the characteristic of the time constant of magnetization reversal with respect to the measurement time of the magnetization pattern of 300/150 kfci.

The characteristic shown in FIG. 18 corresponds to the inverse number of the characteristic shown in FIG. 16. The characteristic shown in FIG. 19 corresponds to the inverse number of the characteristic shown in FIG. 17.

In FIGS. 18 and 19, both the positive data items and the negative data items are indicated. In FIG. 19, the positive data items are plotted as points named "minor bit, increase". The positive data items represent the reversal time constant of the magnetic particles in the bits of 300 kfci.

In FIG. 19, the negative data items are plotted as points named "major bit, decrease" and represent the reversal time constant regarding the bits of 150 kfci. On the other hand, the negative data items are plotted, in FIG. 18, as points named "forward, decrease" and represent the reversal time constant of the magnetic particles of the uniform magnetization.

In FIG. 18, the positive data items are plotted as points named "backward, increase" and represent the time constant for returning to the initial magnetization direction.

In a measurement period (at each period, the measurement time range between a few hours and a few tens of hours), the variation of values of the data items is a little. Thus, the average of the time constants in the period may be defined as a representative value for this period. In the cases shown in FIGS. 18 and 19, the median value is defined as the representative value.

The representative value of the time constants of magnetization reversal regarding in each measurement period is obtained for each pattern.

Figure 20:
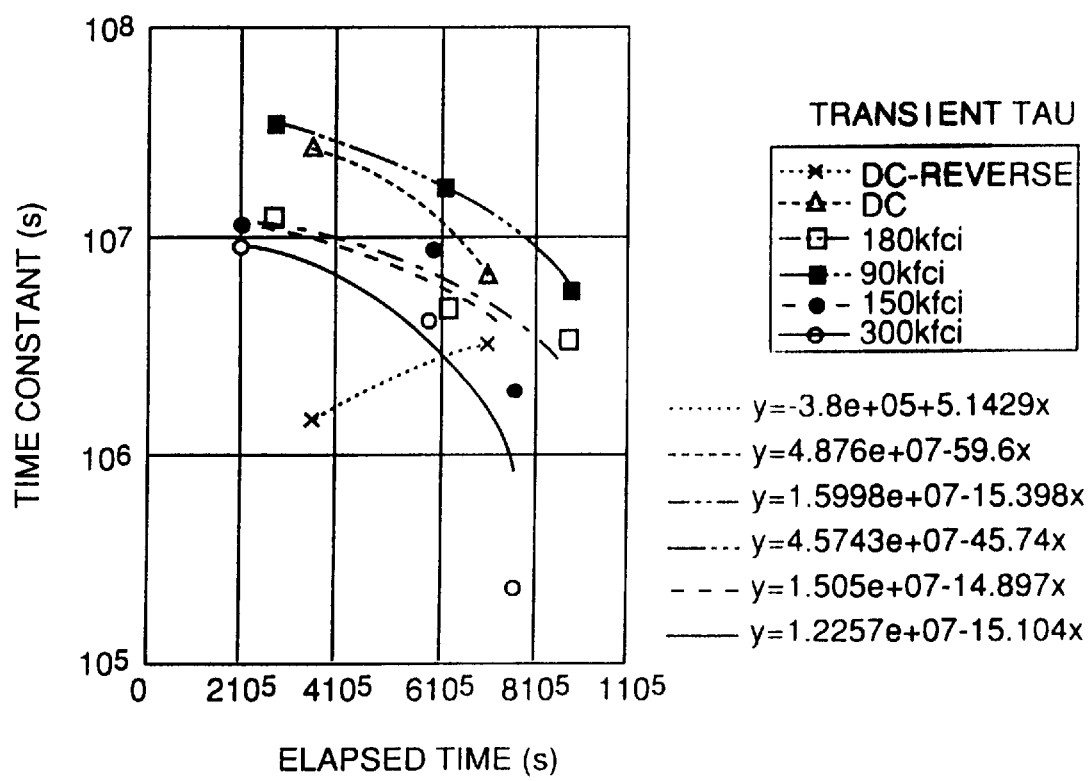
FIG. 20 is a diagram illustrating the summary of the characteristic of the time constant of magnetization reversal with respect to the measurement time in the embodiment of the present invention.

FIG. 20 shows the characteristic of the representative value of time constant of magnetization reversal with respect to the elapsed time.

As shown in FIG. 20, the time constant is decreased with the passage of time in any of the first, second and third recording patterns recorded in the test magnetic recording medium 1. In FIG. 20, symbols x represent the variation of the time constant of magnetic particles in which the magnetizing direction returns to the initial magnetizing direction.

A regression line obtained by the linear approximation based on plotted points is indicated as a curve in a graph having the semi-logarithmic scale shown in FIG. 20. Equations representing the regression lines are shown in FIG. 20.

The extrapolation is carried out, using the equations representing the regression lines, in accordance with the tendency of decreasing of the time constant of magnetization reversal so that a elapsing time corresponding to the reversal time constant of 100 seconds is calculated. In the respective cases of the bit patterns of 300 kfci, 180 kfci, 150 kfci and 90 kfci and the uniform magnetization pattern, elapsed times of "$8.12\times10^5$ [s]", "$1.04\times10^6$ [s]", "$1.01\times10^6$ [s]", "$1.00\times10^6$ [s]" and "$8.18\times10^5$ [s]" are obtained.

Regarding a time when the relaxation of superparamagnetism is accomplished, the dependency on the linear recording density does not appear. During a process to the relaxation of superparamagnetism, the dependency on the linear recording density appears.

A description will now be given of the reduction rate s. In a case shown in FIG. 20, the interpolation is carried out to the respective regression curves so that values of the time constant at the same elapsed time are obtained on the respective regression curves.

At the elapsed time of $4\times10^5$ [s], in the cases of the bit patterns of 300 kfci, 180 kfci, 150 kfci and 90 kfci and the uniform magnetization pattern, the time constant of "$6.22\times10^6$ [s]", "$9.84\times10^6$ [s]", "$9.09\times10^6$ [s]", "$2.74=10^7$ [s]" and "$2.49\times10^7$[S]" are obtained. Thus, in the present cases, the reduction rate s of "0.250", "0.395", "0.365", "1.10" and "1" are obtained. As indicated above, the reduction rate s depends on the linear density.

From the regression equation [$y=1-0.0353\log(t)$] representing the relaxation with respect to the logarithmic scale of time in the second period (the region 2) of the uniform magnetization pattern shown in FIG. 11, the time which elapses until the magnetization is decreased by 10% is obtained. In a case the initial value of the normalized magnetic moment is "0.795" as shown in FIG. 11, by multiplying the respective values of the reduction rate s described above, the life of the bit patterns of 300 kfci, 180 kfci, 150 kfci and 90 kfci and the uniform magnetization pattern are obtained as "$2.87\times10^7$ [s]", "$4.53\times10^7$ [s]", "$4.19\times10^7$ [s]", "$1.26\times10^8$ [s]" and "$1.1\times10^8$ [s]".

FIG. 21 shows the characteristic of the bit record life with respect to the linear recording density which is evaluated.

In the characteristic shown in FIG. 21, there is a tendency for the bit record life to be decreased in accordance with increasing of the linear recording density.

According to the present embodiment, various quantitative scales, depending on the bit linear density, regarding the magnetic relaxation due to the thermal fluctuation can be obtained. Thus, in the development of the high density recording medium, the reliability of the high density recording medium can be evaluated.

In the testing method according to the embodiment of the present invention, any types of hard disk may be the magnetic recording medium to be tested. The material of the magnetic film included in the medium is not limited. It is preferable that the present invention is applied to the magnetic recording medium having a high recording density greater than the linear recording density corresponding to 5 Gbit/in$^2$.

The present invention is not limited to the aforementioned embodiments, and other variations and modifications may be made without departing from the scope of the claimed invention.

What is claimed is:

1. A testing method of a magnetic recording medium which is magnetized, for measuring variation of magnetization with the passage of time and evaluating life of record on said magnetic recording medium, said method comprising the steps of:

(a) recording a first pattern at a linear density to be guaranteed in said magnetic recording medium, said first pattern having a difference between the sum total of areas of +bits and the sum total of areas of −bits;

(b) measuring remanence of said first pattern with the passage of time; and (c) evaluating the life of record on said magnetic recording medium based on a measurement result obtained in step (b).

2. The method as claimed in claim 1, wherein said step (c) comprises the steps of:

(c-1) obtaining a characteristic of transient response of the remanence based on the measurement result; and (c-2) obtaining a time constant of magnetization reversal based on the characteristic transient response of the remanence obtained in said step (c-1), wherein the life of record is evaluated based on the time constant of magnetization reversal obtained in said step (c-2).

3. The method as claimed in claim 2, wherein the time constant of magnetization reversal is obtained in each of a plurality of different periods in said step (c-2), and wherein said step (c) further comprises a step of:

(c-3) measuring variation of the time constant of magnetization reversal with the passage of time in each of said plurality of different periods, wherein the life of record is evaluated based on the variation of the time constant of magnetization reversal with the passage of time in each of said plurality of different periods.

4. A testing method of a magnetic recording medium which is magnetized, for measuring variation of magnetization with the passage of time and evaluating life of record on said magnetic recording medium, said method comprising the steps of:

(a) recording a first pattern and a second pattern in said magnetic recording medium, said first pattern having a difference between the sum total of areas of +bits and the sum total of areas of −bits, said second pattern having a uniform magnetization;

(b) measuring remanence of said first and second patterns with the passage of time; and (c) evaluating the life of record on said magnetic recording medium based on measurement results of the remanence of said first and second patterns obtained in step (b).

5. The method as claimed in claim 4, wherein said step (c) comprises the steps of:

(c-1) obtaining a characteristic of transient response of the remanence of each of said first and second patterns based on the measurement results;

(c-2) obtaining a time constant of magnetization reversal based on the characteristic transient response of the remanence of each of said first and second patterns; and (c-3) obtaining relaxation time of said second pattern, wherein the life of record is evaluated based on a ratio of the time constant of magnetization reversal of the first pattern to the time constant of magnetization reversal of the second pattern and the relaxation time of said second pattern.

6. The method as claimed in claim 5, wherein the time constant of magnetization reversal is obtained in each of a plurality of different periods in step (c-2), and wherein said step (c) further comprises a step of:

(c-4) measuring variation of the time constant of magnetization reversal with the passage of time in each of said plurality of different periods, wherein the variation of the reversal time constant of magnetization reversal with the passage of time in each of said plurality of different periods is used to obtain the life of record.

7. The method as claimed in claim 4, wherein said second pattern is uniform magnetization having a constant magnetizing direction.

8. The method as claimed in claim 4, wherein said first pattern has areas of +bits and areas of −bits which areas are arranged at a frequency based on a density to be guaranteed, the sum total of areas of +bits being equal to the sum total of areas of −bits.

9. A method of measurement of a time constant of magnetization reversal in a magnetized sample, comprising the steps of:

(a) measuring a time-dependent remanence of a bit pattern of the magnetized sample, so that a group of measurement points each of which is defined by a measured residual magnetic moment and a measurement time point are obtained, the group of measurement points indicating a transient tendency of magnetic relaxation of the bit pattern of the magnetized sample;

(b) obtaining a characteristic of transient response to the remanence based on the group of measurement points obtained in said step (a); and (c) obtaining a time constant of magnetization reversal based on the characteristic of transient response of the remanence obtained in said step (b).

10. The method as claimed in claim 9, wherein the time constant of magnetization reversal is obtained in each of a plurality of different periods in said step (c), and wherein said method further comprises a step of:

(e) measuring variation of the time constant of magnetization reversal with the passage of time.

* * * * *

UNITED STATES PATENT AND TRADEMARK OFFICE
CERTIFICATE OF CORRECTION

PATENT NO. : 6,147,488  
DATED : November 14, 2000  
INVENTOR(S) : Bamba et al.

Page 1 of 1

It is certified that error appears in the above-identified patent and that said Letters Patent is hereby corrected as shown below:

<u>Claim 9,</u>  
Line 6, delete "points each" and insert -- points, each -- therefor.  
Line 7, delete "moment and" and insert -- moment, and -- therefor.

Signed and Sealed this

First Day of January, 2002

Attest:

Attesting Officer

JAMES E. ROGAN  
*Director of the United States Patent and Trademark Office*